US009883815B2

(12) United States Patent
Einarsson et al.

(10) Patent No.: US 9,883,815 B2
(45) Date of Patent: Feb. 6, 2018

(54) ELECTROMYOGRAPHY WITH PROSTHETIC OR ORTHOTIC DEVICES

(71) Applicant: Össur Iceland ehf, Reykjavík (IS)

(72) Inventors: Árni Einarsson, Reykjavík (IS); Stefán Páll Sigurpórsson, Reykjavik (IS); Atli Örn Sverrisson, Reykjavík (IS)

(73) Assignee: Össur Iceland ehf, Reykjavik (IS)

( * ) Notice: Subject to any disclaimer, the term of this patent is extended or adjusted under 35 U.S.C. 154(b) by 122 days.

(21) Appl. No.: 15/132,015

(22) Filed: Apr. 18, 2016

(65) Prior Publication Data

US 2016/0302686 A1    Oct. 20, 2016

Related U.S. Application Data

(60) Provisional application No. 62/150,162, filed on Apr. 20, 2015.

(51) Int. Cl.
*A61F 2/66* (2006.01)
*A61F 2/72* (2006.01)
(Continued)

(52) U.S. Cl.
CPC ............ *A61B 5/04888* (2013.01); *A61F 2/60* (2013.01); *A61F 2/72* (2013.01); *A61F 2/66* (2013.01); *A61F 2/6607* (2013.01); *A61F 2002/701* (2013.01); *A61F 2002/704* (2013.01); *A61F 2002/705* (2013.01); *A61F 2002/764* (2013.01); *A61F 2002/7625* (2013.01)

(58) Field of Classification Search
None
See application file for complete search history.

(56) References Cited

U.S. PATENT DOCUMENTS

| 4,030,141 A | 6/1977 | Graupe |
| 5,193,539 A | 3/1993 | Schulman et al. |

(Continued)

FOREIGN PATENT DOCUMENTS

| EP | 1508302 | 2/2005 |
| EP | 1666091 | 8/2006 |

(Continued)

OTHER PUBLICATIONS

International Search Report in International Application No. PCT/US2016/028166 dated Aug. 29, 2016.

(Continued)

*Primary Examiner* — David H Willse
(74) *Attorney, Agent, or Firm* — Knobbe Martens Olson & Bear LLP

(57) ABSTRACT

Systems, devices and methods for control of a prosthetic or orthotic device (POD) based on electromyography (EMG) signals are described. The POD may be a lower or upper limb POD having one or more joints. One or more EMG sensors may detect the EMG signals. The EMG sensors may be external, subcutaneous, intraperitoneal, epimysial, intramuscular, or other types. Control of the POD may be based on EMG and non-EMG signals, such as velocity, acceleration, position, force, etc. Voluntary and/or automatic control may be implemented, for example with voluntary muscle contractions and/or data based on velocity, acceleration, position, force, etc. In some embodiments, the neutral position of an ankle POD is adjusted based on EMG signals.

26 Claims, 13 Drawing Sheets

(51) Int. Cl.
*A61B 5/0488* (2006.01)
*A61F 2/60* (2006.01)
*A61F 2/70* (2006.01)
*A61F 2/76* (2006.01)

(56) References Cited

U.S. PATENT DOCUMENTS

| | | | |
|---|---|---|---|
| 5,193,540 | A | 3/1993 | Schulman et al. |
| 5,312,439 | A | 5/1994 | Loeb |
| 5,314,458 | A | 5/1994 | Najafi et al. |
| 5,314,495 | A | 5/1994 | Kovacs |
| 5,324,316 | A | 6/1994 | Schulman et al. |
| 5,336,269 | A | 8/1994 | Smits |
| 5,358,514 | A | 10/1994 | Schulman et al. |
| 5,405,367 | A | 4/1995 | Schulman et al. |
| 5,522,865 | A | 6/1996 | Schulman et al. |
| 5,711,307 | A | 1/1998 | Smits |
| 5,876,425 | A | 3/1999 | Gord et al. |
| 6,164,284 | A | 12/2000 | Schulman et al. |
| 6,185,452 | B1 | 2/2001 | Schulman et al. |
| 6,208,894 | B1 | 3/2001 | Schulman et al. |
| 6,564,807 | B1 | 5/2003 | Schulman et al. |
| 6,587,728 | B2 | 7/2003 | Fang et al. |
| 6,610,101 | B2 | 8/2003 | Herr et al. |
| 6,666,214 | B2 | 12/2003 | Canham |
| 6,695,885 | B2 | 2/2004 | Schulman et al. |
| 6,764,520 | B2 | 7/2004 | Deffenbaugh et al. |
| 6,839,596 | B2 | 1/2005 | Nelson et al. |
| 6,990,372 | B2 | 1/2006 | Perron et al. |
| 7,024,249 | B2 | 4/2006 | Weisner et al. |
| 7,058,445 | B2 | 6/2006 | Kemere et al. |
| 7,114,502 | B2 | 10/2006 | Schulman et al. |
| 7,147,667 | B2 | 12/2006 | Bedard |
| 7,235,050 | B2 | 6/2007 | Schulman et al. |
| 7,314,490 | B2 | 1/2008 | Bedard et al. |
| 7,460,911 | B2 | 12/2008 | Cosendai et al. |
| 7,565,204 | B2 | 7/2009 | Matei |
| 7,637,959 | B2 | 12/2009 | Clausen et al. |
| 7,736,394 | B2 | 6/2010 | Bedard et al. |
| 7,811,334 | B2 | 10/2010 | Ragnarsdottir et al. |
| 7,896,927 | B2 | 3/2011 | Clausen et al. |
| 7,908,014 | B2 | 3/2011 | Schulman et al. |
| 7,979,140 | B2 | 7/2011 | Schulman |
| 8,007,544 | B2 | 8/2011 | Jonsson et al. |
| 8,155,745 | B1 | 4/2012 | Merrill et al. |
| 8,176,922 | B2 | 5/2012 | Sherman et al. |
| 8,435,309 | B2 | 5/2013 | Gilbert et al. |
| 8,828,093 | B1 | 9/2014 | Kuiken et al. |
| 8,900,325 | B2 | 12/2014 | Herr et al. |
| 8,926,534 | B2 | 1/2015 | McBean et al. |
| 9,017,418 | B2 | 4/2015 | Clausen |
| 9,066,819 | B2 | 6/2015 | Gramnaes |
| 9,078,774 | B2 | 7/2015 | Jonsson et al. |
| 9,114,030 | B2 | 8/2015 | Van der Merwe et al. |
| 9,121,699 | B2 | 9/2015 | Van der Merwe et al. |
| 9,221,177 | B2 | 12/2015 | Herr et al. |
| 9,289,316 | B2 | 3/2016 | Ward et al. |
| 2005/0104577 | A1 | 5/2005 | Matei et al. |
| 2006/0015470 | A1 | 1/2006 | Lauer et al. |
| 2006/0224246 | A1 | 10/2006 | Clausen et al. |
| 2006/0235488 | A1 | 10/2006 | Nycz et al. |
| 2008/0071386 | A1 | 3/2008 | McBeam et al. |
| 2010/0016990 | A1 | 1/2010 | Kurtz |
| 2011/0125290 | A1 | 5/2011 | Langlois |
| 2012/0004736 | A1 | 1/2012 | Goldfarb |
| 2012/0101596 | A1 | 4/2012 | Dietl |
| 2012/0109256 | A1 | 5/2012 | Meskins et al. |
| 2012/0259388 | A1 | 10/2012 | Galvan-Garcia |
| 2012/0316620 | A1 | 12/2012 | Suaning et al. |
| 2012/0316622 | A1 | 12/2012 | Whitehurst et al. |
| 2014/0031952 | A1 | 1/2014 | Harshbarger et al. |
| 2014/0088379 | A1 | 3/2014 | Irazoqui et al. |
| 2014/0128992 | A1 | 5/2014 | Engeberg |
| 2015/0073566 | A1 | 3/2015 | Ragnarsdottir et al. |

FOREIGN PATENT DOCUMENTS

| | | |
|---|---|---|
| EP | 1508299 | 4/2013 |
| WO | WO1998043701 | 10/1998 |
| WO | WO2002031909 | 4/2002 |
| WO | WO2003000161 | 1/2003 |
| WO | WO2004073491 | 9/2004 |
| WO | WO 2006/098790 | 9/2006 |
| WO | WO2006098791 | 12/2007 |

OTHER PUBLICATIONS

U.S. Appl. No. 10/742,455, filed Jun. 23, 2005, Gramnas et al.
U.S. Appl. No. 11/077,177, filed Dec. 22, 2005, Bisbee et al.
U.S. Appl. No. 13/754,298, filed Jun. 6, 2013, Clausen et al.
U.S. Appl. No. 13/767,945, filed Aug. 22, 2013, Holgate, Matthew Aaron.
U.S. Appl. No. 14/206,956, filed Sep. 18, 2014, Clausen, Arinbjorn.
Kirchner, Elsa Andrea et al., *Closing the Gap: Combined EEG and EMG Analysis for Early Movement Prediction in Exoskeleton based Rehabilitation*, Technically Assisted Rehabilitation (TAR) 4th Conference, Session 4 (Mar. 14-15, 2013, Berlin).
Oddsson, Magnus, *Advanced Control for Bionic Leg Systems*, Technically Assisted Rehabilitation (TAR) 4th Conference, Session 10 (Mar. 14-15, 2013, Berlin).
Paredes, Liliana, et al., *Towards Robustness in Pattern Recognition Based Myoelectric Prosthesis Control*, Technically Assisted Rehabilitation (TAR) 4th Conference, Session 4 (Mar. 14-15, 2013, Berlin).
Schwartz, David. *Purdue inks license for technology to drastically improve prosthetic limb control for amputees*, Tech Transfer eNews Blog, Mar. 16, 2016 (available at http://techtransfercentral.com/2016/03/16/purdue-inks-license-for-technology-to-drastically-improve-prosthetic-limb-conrol-for-amputees/) (last accessed on Apr. 27, 2016).
Soekadar, Surjo R. et al., *Control of a hand-exoskeleton using a Brain/Neuronal Computer Interaction (BNCI) System*, Technically Assisted Rehabilitation (TAR) 4th Conference, Session 4 (Mar. 14-15, 2013, Berlin).
Klauer, Christian, et al., Advanced Control Strategies for Neuro-Prosthetic Systems, Technically Assisted Rehabilitation (TAR) 4th Conference, Session 5 (Mar. 14-15, 2013, Berlin).
Miller et al., "Myoelectric walking mode classification for transtibial amputees", IEEE Trans Biomed Eng. Oct. 2013; 60(10):2745-50. doi: 10.1109/TBME.2013.2264466 Epub May 21, 2013.

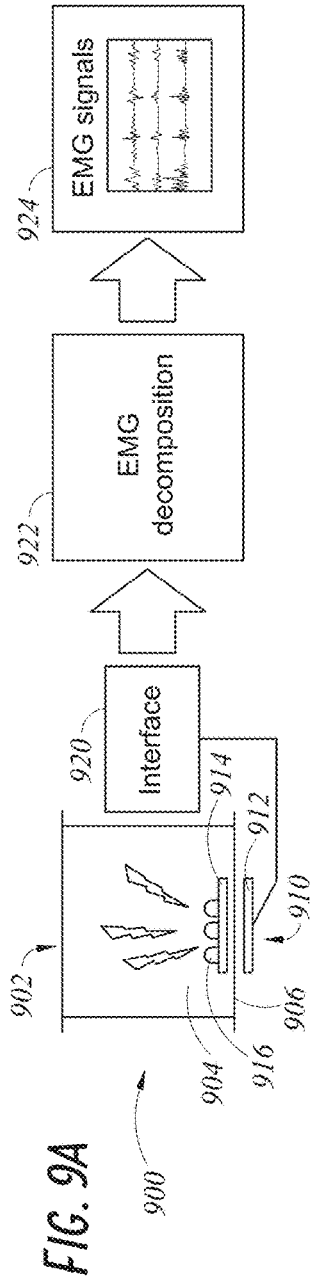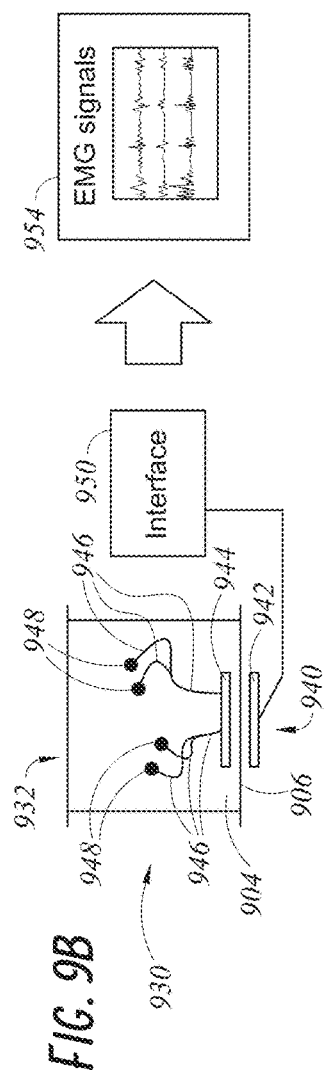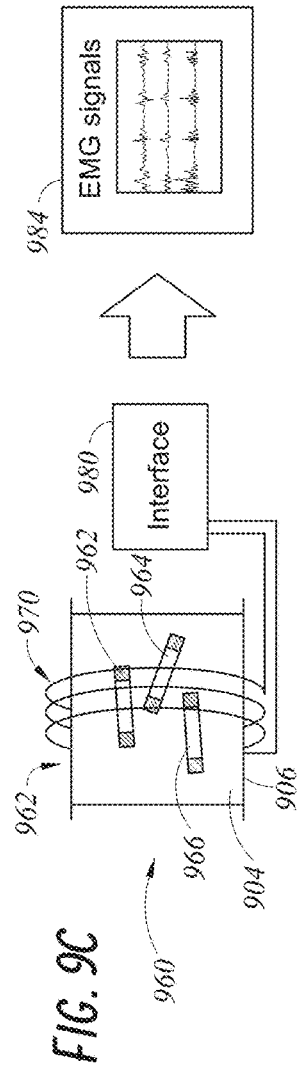
FIG. 9A
FIG. 9B
FIG. 9C

ELECTROMYOGRAPHY WITH PROSTHETIC OR ORTHOTIC DEVICES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit of U.S. Provisional Patent Application No. 62/150,162, filed Apr. 20, 2015, entitled ELECTROMYOGRAPHY WITH PROSTHETIC OR ORTHOTIC DEVICES, the disclosure of which is incorporated herein by reference in its entirety for all purposes.

BACKGROUND

Field

This disclosure relates generally to prosthetic or orthotic devices ("PODs"). In particular, embodiments disclosed herein generally relate to the use of electromyography ("EMG") with prosthetic or orthotic devices ("PODs").

Description of the Related Art

Various types of prosthetic and orthotic devices are available as artificial substitutes for a missing body part or as additions to existing limbs, such as an arm or leg. Prosthetic and orthotic joints are also available as substitutes or augmentations for human joints, such as an ankle or knee. Electronically controlled prosthetic and orthotic devices, such as "mechatronic" devices, can provide safer and more natural movement. Improvements to control systems for such mechatronic devices could advantageously allow the devices to more closely approximate the movement of natural joints and provide users with a greater range of motion and greater stability. Therefore, a need exists for improved approaches to controlling robotic limbs and devices that overcome or minimize the above-referenced problems.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for PODs.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

In some embodiments, the POD can be a lower-limb prosthesis. The lower-limb prosthesis can comprise a controller, memory, and sensor-set. A person having ordinary skill in the art should appreciate that aspects of this disclosure can be used in any prosthetic, including hip, hand, wrist, arm, any upper extremity prostheses, any lower extremity prostheses, and/or any type of prosthetic device. Certain aspects of this disclosure can be particularly desirable to optimize devices having an actuator, wherein control of the actuator can be based at least in part on data obtained from one or more sensors, such as EMG sensors. This data can be a raw measurement taken by the sensor, an amplified, aggregated or otherwise processed set of measurements taken by the sensor and/or any other information signal. The information provided by the sensors (e.g., EMG) can be used to improve performance and acceptability of the operation of the actuatable device.

In a first aspect, a system for controlling a prosthetic or orthotic device (POD) is described. The system comprises a first limb member, a second limb member coupled to the first member, the first limb member and the second limb member forming a joint having a neutral position that is used throughout a gait cycle to adjust a joint angle between the first limb member and the second limb member, at least one first sensor configured to measure electromyography (EMG) signals from a first muscle over a period of time, a controller configured to receive a first EMG signal from the at least one first sensor and to determine an adjusted neutral position based at least in part on the first EMG signal, and at least one actuator communicatively coupled to the controller, the at least one actuator configured to actuate the first limb member with respect to the second limb member such that the adjusted neutral position is used throughout the gait cycle to adjust the joint angle between the first limb member and the second limb member.

In some embodiments, the system further comprises at least one second sensor configured to measure EMG signals from a second muscle over the period of time, and the controller is further configured to receive a second EMG signal from the at least one second sensor and to determine an adjusted neutral position based at least in part on the first EMG signal and the second EMG signal. In some embodiments, the first muscle is antagonistic to the second muscle. In some embodiments, the at least one first sensor is an external sensor, a subcutaneous sensor, an intraperitoneal sensor, an epimysial sensor, or an intramuscular sensor. In some embodiments, the at least one first sensor is an external sensor, a subcutaneous sensor, an intraperitoneal sensor, an epimysial sensor, or an intramuscular sensor, and the at least one second sensor is an external sensor, a subcutaneous sensor, an intraperitoneal sensor, an epimysial sensor, or an intramuscular sensor. In some embodiments, the joint is an ankle joint and the joint angle is an ankle angle. In some embodiments, the controller is configured to determine the adjusted neutral position in response to determining that the first EMG signal was produced by one or more voluntary contractions of the first muscle. In some embodiments, the joint is an ankle joint, and the controller is configured to determine a plantar-flexion movement or a powered plantar-flexion movement of the ankle joint based at least in part on the first EMG signal. In some embodiments, the controller is configured to determine a first state has been entered based at least in part on the first EMG signal, and the controller is configured to automatically effect the plantar-flexion movement or the powered plantar-flexion movement of the ankle joint after entering the first state. In some embodiments, the first state is running or stair descent. In some embodiments, the controller is configured to determine the adjusted neutral position based on comparison of the first EMG signal with one or more thresholds. In some embodiments, the one or more thresholds is one or more of amplitude, frequency, envelope, or rate of change. In some embodiments, the controller is configured to determine the adjusted neutral position based on comparison of the first EMG signal with previous EMG signals from previous steps. In some embodiments, the controller is configured to determine the adjusted neutral position based on a time series analysis of the first EMG signal. In some embodiments, the controller is configured to determine a target position based on the adjusted neutral angle according to the following equation, wherein the first muscle is MuscleX and the second muscle is MuscleY: Postarget=Posneutral=Poscurrent+ (MuscleXsignal*MuscleXgain+MuscleXoffset− MuscleYsignal*MuscleYgain+MuscleYoffset).

In another aspect, another system for controlling a prosthetic or orthotic device (POD) is described. The system comprises a first limb member, a second limb member coupled to the first member, the first limb member and the second limb member forming a joint having a neutral position that is used throughout a gait cycle to adjust a joint angle between the first limb member and the second limb member, at least one sensor configured to measure electromyography (EMG) signals associated with a muscle over a period of time, a controller configured to receive the EMG signal and to determine an adjusted neutral position based at least in part on at least the EMG signal and to select a control mode for POD motion from a plurality of control modes based at least in part on at least the EMG signal, and at least one actuator communicatively coupled to the controller, the at least one actuator configured to actuate the POD based at least in part on the control mode for POD motion and to actuate the first limb member with respect to the second limb member such that the adjusted neutral position is used throughout the gait cycle to adjust the joint angle between the first limb member and the second limb member.

In some embodiments, the control mode for POD motion is at least one of activation, stair ascent, stair descent, ramp ascent, ramp descent, golfing, biking, Nordic walking, walking, jogging, running or kicking. In some embodiments, the joint is an ankle joint. In some embodiments, the EMG signals are associated with voluntary contraction of the muscle. In some embodiments, the joint is an ankle joint, and the controller is configured to determine a plantar-flexion movement or a powered plantar-flexion movement of the ankle joint based at least in part on the first EMG signal. In some embodiments, the controller is configured to automatically effect the plantar-flexion movement or the powered plantar-flexion movement of the ankle joint while in the first mode. In some embodiments, the controller is configured to determine the adjusted neutral position in response to determining that the first EMG signal was produced by one or more voluntary contractions of the first muscle.

In another aspect, a system for controlling a prosthetic or orthotic device (POD) is described. The POD includes a first limb member and a second limb member forming an ankle joint having a neutral position that is used throughout a gait cycle to adjust an ankle joint angle. The system comprises at least one first sensor configured to be implanted in a muscle and to measure myoelectric signals from the muscle over a period of time and to transmit an electromyography (EMG) signal generated at least in part from the measured myoelectric signals from the muscle, at least one second sensor configured to measure at least one of acceleration, angle, force, and velocity over the period of time and to transmit an information signal generated at least in part from the at least one of acceleration, angle, force, and velocity, a controller configured to receive the EMG signal and the information signal, based at least in part on a determination that the EMG signal does not satisfy an EMG signal threshold, generate a control signal according to a first control scheme, wherein the first control scheme is based at least in part on the information signal, based at least in part on a determination that the EMG signal satisfies the EMG threshold, generate the control signal according to a second control scheme, where the second control scheme is based at least in part on the information signal and the EMG signal, and determine an adjusted neutral position of the ankle joint based at least in part on the EMG signal, and at least one actuator coupled to the controller, the at least one actuator configured to actuate the POD based at least in part on the control signal and on the adjusted neutral angle.

In some embodiments, the controller is further configured to determine the control signal based on either the EMG signal or the information signal, where the controller chooses between the EMG signal and the information signal based at least in part on the relative amplitudes of the EMG signal and the information signal. In some embodiments, the controller is further configured to determine the control signal based on either the EMG signal or the information signal, where the controller chooses between the EMG signal and the information signal based at least in part on the relative frequency of the EMG signal and the information signal. In some embodiments, the controller generated control signal comprises information derived from the EMG signal and the information signal.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 9A-9C are schematics illustrating embodiments of particular EMG sensor and analysis systems, including a subcutaneous system, a hub and electrode system, and a coil system, that can be used by the various control systems herein to control the various PODs described herein.

DETAILED DESCRIPTION

Figure 1A:
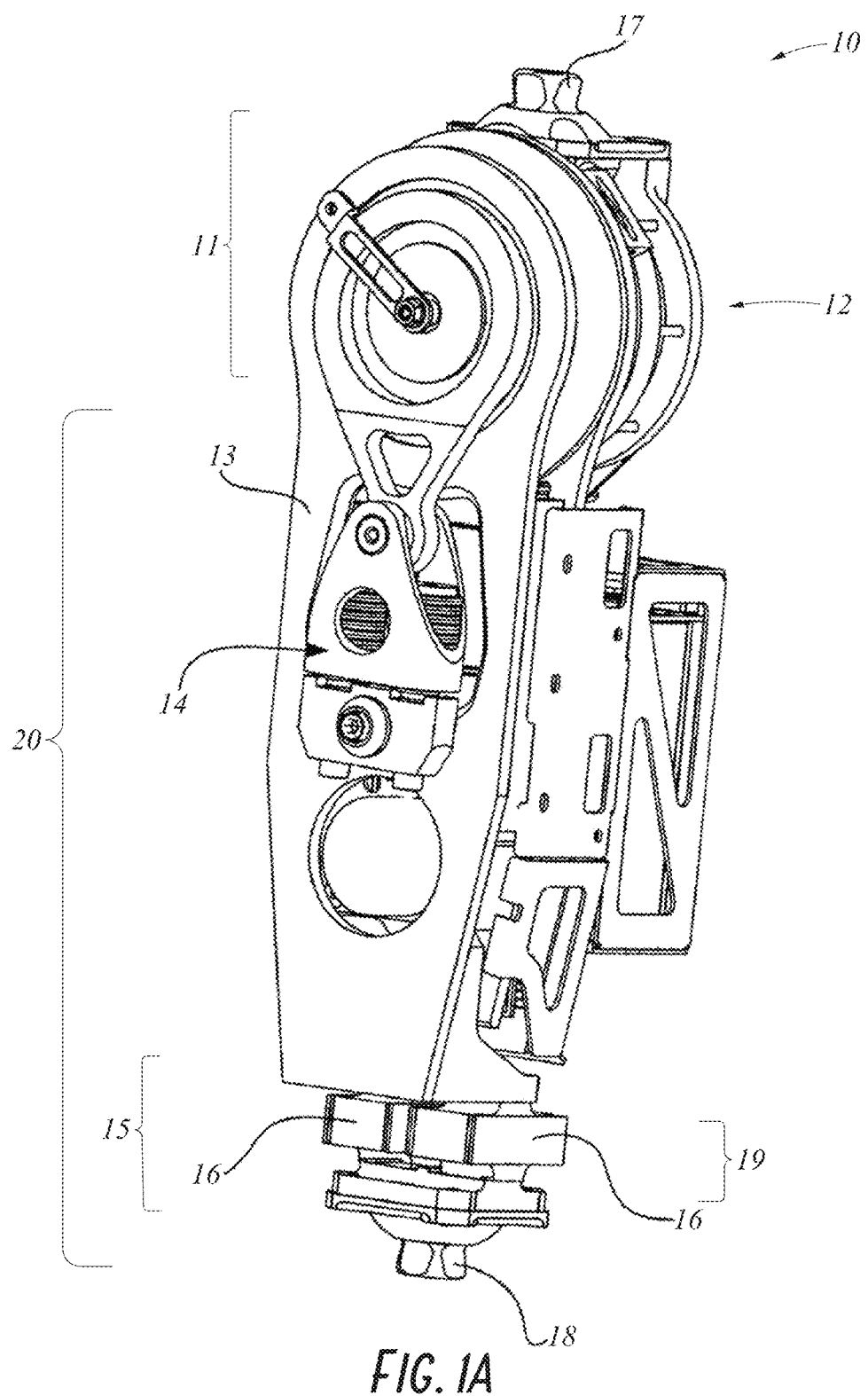
FIG. 1A is a perspective view of an embodiment of an EMG-controllable prosthetic or orthotic device ("POD") shown as a lower-limb POD having a knee joint and shank segment.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Described herein are systems for and methods of using electromyography ("EMG") with prosthetic or orthotic devices ("PODs"). EMG is used broadly herein to refer to sensors, techniques, devices, etc. that sense or otherwise use the electrical activity or signals generated by any muscle of the human body. This includes the use of, for example, sensors and techniques for an electromyogram, for surface EMG, for intramuscular EMG, or for implanted EMG sensors, etc. The sensors may thus be an external sensor, a subcutaneous sensor, an intraperitoneal sensor, an epimysial sensor, an intramuscular sensor, etc.

The EMG signals can include electrical signals such as myoelectric signals as well as motor action potentials, muscle potentials, M-waves, and/or any electrical signal (and/or electrical impulse) associated with a muscle, or any signal associated with EMG, or any signal derived from the aforementioned signals. The sensors or devices can communicate either wirelessly or by wire with a controller and/or communication interface of the POD.

The term "muscle" is used broadly herein and includes any neuroskeletal muscles (sometimes called "skeletal muscle" or "striated muscle tissue") of the human body. This can include, for example, muscles of the leg, arm, back, or any other body part.

POD is used broadly herein and refers to any prosthetic and/or orthotic device for a human body, whether upper, lower or other body parts. This includes, for example, arms, legs, hip, hand, wrist, arm, any upper extremity prostheses, any lower extremity prostheses, or any other types. The POD may include one or more joints. For, example it may include a lower-limb prosthesis with knee and/or ankle joints, a lower-leg prosthetic device having only an ankle joint, etc. The joints may be actuatable, for example by an actuator, such as a motor. POD also includes orthotics, such as exoskeletons and other assistive devices.

The POD may also include a controller, a memory, and a sensor. The POD, such as the controller or a communication interface, may be in wireless or wired communication with the EMG sensors in order to control or otherwise affect the POD based on information from the EMG sensors. For example, the actuator may move a joint, or provide resistance to a joint, etc. based on feedback from the sensors. As another example, various parameters may be adjusted, such as neutral angles, etc.

There may be multiple POD's or POD portions in communication with each other. For example, there may be two POD's where the sensors and/or controllers of a first POD associated with one limb communicate with sensors and/or controllers of a second POD associated with a second limb. As another example, sensors and/or controllers of different portions of the same POD can communicate with each other.

Other measurements can also be taken with and/or in conjunction with the EMG. For example, measurements of electrical signals associated with nerves, including nerve conduction, nerve potential, neurological signals, nerve action potential; other physical parameters, such as temperature, blood pressure, oxygenation, blood flow; characteristics of motion of the user and/or POD, such as acceleration, inertia, velocity, angle; position and orientation of the POD, such as displacement or angle relative to ground, joint angle, joint moment, ground force, and the like. Such sensors can comprise any one or any combination of inertial sensors, gyroscopes, accelerometers, angle sensors, magnetometers, etc. Further, these and other measurements may be taken from the same portion of the body on which the POD is located, and/or from a different portion of the body on which the POD is located.

The EMG and other measurements are used to affect the POD. Any of the measurements may be processed, for example by the controller, and used, for example to control, the POD. Such controls may affect the response (e.g. drive) of an actuator. Actuator responses can be based on the EMG signals in a variety of ways, for example the actuator response may be proportional to characteristics of a measured EMG signal such as amplitude (minimum, maximum, average, etc.), frequency, response time, rate of change, etc.

Various aspects of the POD may be affected, such as knee and/or ankle positions, angle, velocity, acceleration, moment/torque, etc.

The POD may be controlled using dynamic scaling of EMG measurements taken over time. For example, short and/or long term changes in the measurements may be analyzed, patterns may be recognized, etc. This may be due, for example, to muscle fatigue, muscle growth, etc. The controller can account for such changes, for example by amplifying the signal with gains greater or less than unity.

The POD may be directly controlled. For example, muscle contractions can directly control an actuator associated with a joint. For instance, activation of an upper leg muscle can control lower leg POD actuation for the same leg.

The POD may be controlled based on sensing the entering into certain phases. For example, the EMG sensors may detect stance, sitting down, or stair descent, stair ascent, etc. These or other detected phases may be used to control a variety of parameters, such as a target swing extension angle for a joint, etc.

The POD may be controlled by enabling usage modes by contracting muscles in a pattern. For instance, various modes may be entered by contracting a muscle a predetermined number of times within a set period of time, for a predetermined length of time or intensity, contracting muscles in a certain sequence, clicking a muscle, etc. These or other techniques may cause the POD to enter various modes, such as stair ascent or descent, ramp ascent or descent, pre-programmed modes (e.g. Golfing, biking, Nordic walking, etc.), or other modes.

The POD may be controlled involuntarily. For example, EMG signals can be monitored during regular gait, and certain gait events can be identified based at least in part on EMG signal patterns. As another example, known transitions may be used. For instance, the POD can store in memory EMG signal patterns corresponding to transitions such as stance-to-swing, or others.

The POD motion may be controlled based on relative amplitudes and/or manner of muscle activation. For instance, a target position for a POD, such as a knee or ankle joint, may be based on a neutral position and gain and offset factors.

Various joints can be controlled in a variety of manners based on the EMG information. Using an ankle as an example, the ankle joint may controlled: using voluntary velocity control (e.g. the joint flexes faster with higher EMG magnitude); while ambulating with muscle activation (e.g. changing the neutral position of an ankle based on detected terrain); auto control of ankle while ambulating (e.g. performing toe-lift while ambulating for safety); control of ankle while non-ambulating using muscle activation (e.g. to dorsi-flex the ankle joint to stand up from a chair more easily); or other manners described herein.

The system may incorporate artificial intelligence (AI) training. For example, AI can be trained to associate EMG signals and/or other measurements with certain activities. The AI can monitor sensors during those activities in order to learn to associate patterns in the signals from those sensors with the activities. For example, an AI can know that a user is ascending stairs based at least in part on measurements taken by a gyroscope.

In some embodiments, the neutral position or angle of a POD joint, such as an ankle joint, may be adjusted based at least in part on EMG signals. The neutral position may be a position typically used throughout a gait cycle to adjust a joint angle between the first limb member and the second limb member. The actuator may be configured to actuate the first limb member with respect to the second limb member such that an adjusted neutral position is instead used throughout the gait cycle to adjust the joint angle between the first limb member and the second limb member. In some embodiments, the controller is configured to determine the adjusted neutral position in response to determining that the first EMG signal was produced by one or more voluntary contractions of the first muscle. The joint may be an ankle joint, and the controller may be configured to determine a plantar-flexion movement or a powered plantar-flexion movement of the ankle joint based at least in part on the first EMG signal. The controller may be configured to determine a first state has been entered based at least in part on the first EMG signal and to automatically effect the plantar-flexion movement or the powered plantar-flexion movement of the ankle joint after entering the first state and/or while in the first state and/or until the first state has been exited. Thus, a "bi-modal" control technique may be implemented, as described herein, for example where voluntary contraction of a muscle initially effects the plantar-flexion or powered plantar-flexion and thereafter the plantar-flexion or powered plantar-flexion is effected automatically, such as during a particular state following the voluntary contraction.

Figure 1B:
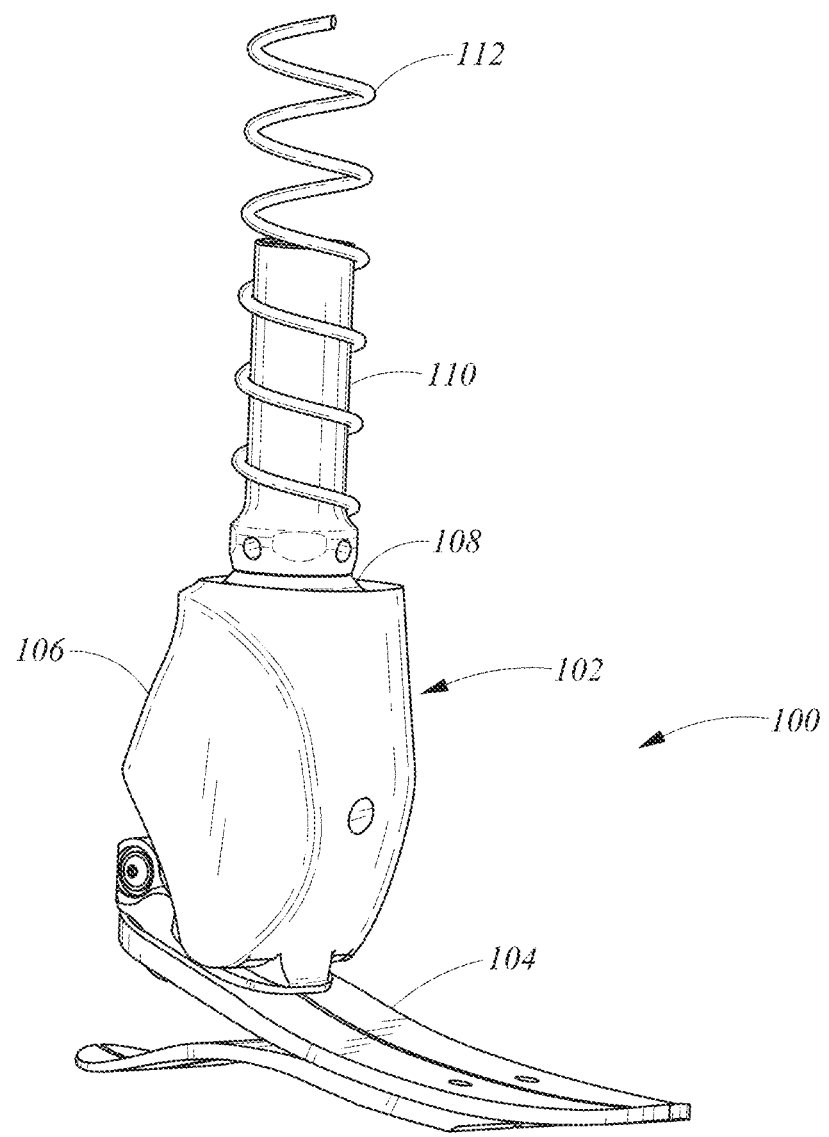
FIG. 1B is a perspective view of an embodiment of an EMG-controllable POD shown as a lower-limb POD having an ankle and foot unit.
Figure 2:
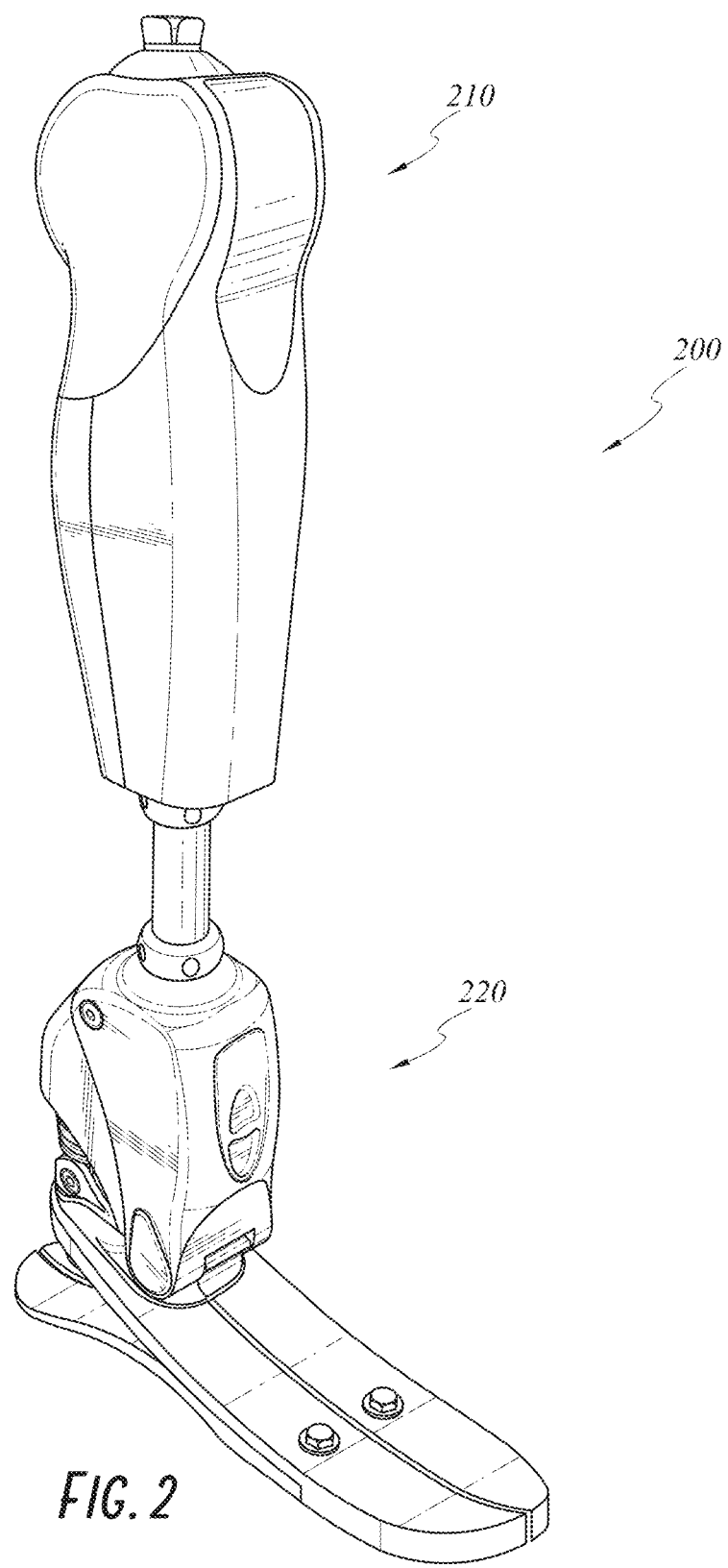
FIG. 2 is a perspective view of an embodiment of an EMG-controllable POD shown as a lower-limb POD having a knee joint, shank segment and an ankle and foot unit.

FIG. 1A is a perspective view of an embodiment of a POD 10 shown as a lower-limb POD having an actuatable knee joint 11 and shank segment 20. FIG. 1B is a perspective view of an embodiment of a POD 100 shown as a lower-limb POD having an ankle and foot unit 104 with an attachment member 102. FIG. 2 is a perspective view of an embodiment of a POD 200 shown as a lower-limb POD having a knee and shank component 210 coupled with an ankle and foot component 220. The PODs 10, 100 and 200 may be used with the various EMG devices, systems and methods described herein. The PODs 10, 100 and 200 may have the same or similar features and/or functionalities as the POD features and functionalities as described, for example, in U.S. Pat. No. 8,435,309, issued May 7, 2013, and entitled JOINT ACTUATION MECHANISM FOR A PROSTHETIC AND/OR ORTHOTIC DEVICE HAVING A COMPLIANT TRANSMISSION, in U.S. Pat. No. 7,811,334, issued Oct. 12, 2010, and entitled SYSTEM AND METHOD FOR MOTION-CONTROLLED FOOT UNIT, in U.S. Pat. No. 7,896,927, issued Mar. 1, 2011, and entitled SYSTEMS AND METHODS FOR ACTUATING A PROSTHETIC ANKLE BASED ON A RELAXED POSITION, in U.S. Pat. No. 7,637,959, issued Dec. 29, 2009, and entitled SYSTEMS AND METHODS FOR ADJUSTING THE ANGLE OF A PROSTHETIC ANKLE BASED ON A MEASURED SURFACE ANGLE, in U.S. Pat. No. 6,764,520, issued Jul. 20, 2004, and entitled ELECTRONICALLY CONTROLLED PROSTHETIC KNEE, in U.S. Pat. No. 6,610,101, issued Aug. 26, 2003, and entitled SPEED-ADAPTIVE AND PATIENT-ADAPTIVE PROSTHETIC KNEE, in U.S. patent application Ser. No. 11/077,177, filed Mar. 9, 2005, and entitled CONTROL SYSTEM AND METHOD FOR A PROSTHETIC KNEE, in U.S. Pat. No. 7,314,490, issued Jan. 1, 2008, and entitled ACTUATED LEG PROSTHESIS FOR ABOVE-KNEE AMPUTEES, in U.S. Pat. No. 7,736,394, issued Jun. 15, 2010, and entitled ACTUATED PROSTHESIS FOR AMPUTEES, in U.S. Pat. No. 7,147,667, issued Dec. 12, 2006, and entitled CONTROL SYSTEM AND METHOD OF CONTROLLING AN ACTUATED PROSTHESIS, in U.S. Pat. No. 8,435,309, issued May 7, 2013, and entitled JOINT ACTUATION MECHANISM FOR A PROSTHETIC AND/OR ORTHOTIC DEVICE HAVING A COMPLIANT TRANS- MISSION, in U.S. Patent Application Publication No. 2011/0125290, filed on Jan. 21, 2008, and entitled REACTIVE LAYER CONTROL SYSTEM FOR PROSTHETIC AND ORTHOTIC DEVICES, and/or in U.S. patent application Ser. No. 13/754,298, filed Jan. 30, 2013, and entitled "TRANSFEMORAL PROSTHETIC SYSTEMS AND METHODS FOR OPERATING THE SAME," the entirety of each which is hereby incorporated by reference herein for all purposes and is to be considered as part of this specification.

Some features of the PODS 10, 100, 200 will now be described. This is just a description of examples of some of the features. The references incorporated herein disclose additional details that may apply to any of the PODs 10, 10, 200 or aspects thereof, whether related to structure, function, or other aspects of human amputees using PODs, including but not limited to gait cycles of normal walking, running, etc., movement of a POD during walking, running etc., and any background information on dynamic, kinetic, kinematic, and other general principles related to normal human limb motion and motion of a POD.

FIG. 1A is a perspective view of an embodiment of a POD 10 that may be controlled with the various EMG systems described herein. The POD 10 or one or more portions thereof may be controlled with EMG based systems as described herein. The POD 10 is a lower-limb POD having a knee joint 11 and shank segment 20. The POD 10 includes a proximal connector 17 sitting on top of an actuator 12 which is mounted at the knee joint 11 level. The proximal connector 17 is configured to be connected to a socket (not shown) that is mountable to the leg stump, e.g., a thigh, of a user. The socket can be placed over or around the leg stump, or be grafted to the tissue of the user. The proximal connector 17, the actuator 12, and the knee joint level 11 can form a thigh segment of the POD 10.

The shank segment 20 of the POD 10 can include a shank structure 13, such as a tibial member extending downward from the proximal connector that is rotatable via the actuator 12 relative to the proximal connector 17. In this example, the actuator 12 may be, for example, a DC brushless motor serially connected to a reduction mechanism. The reduction mechanism of the actuator 12 allows the conversion of the motor high-speed, low torque output characteristics into a low-speed, high-torque output that is more coherent with the requirements associated with the human knee joint role in most commonly encountered locomotor tasks. A second transmission stage is then provided in order to connect the reduction mechanism output to the shank structure 13 of the motorized knee POD 10. This second transmission stage is composed of a compliant linkage 14, allowing both measurement of the net torque present at the interface between the shank structure 13 and the actuator 12 output and high-efficiency level walking stance flexion energy storage and return.

A load cell assembly 19 containing one or more load cells 16 can be located at the distal shank portion 15 between the shank structure 13 and the distal connector 18 of the POD 10 to quantify the load found in the distal shank portion 15. The distal connector 18 is configured to connect to a prosthetic ankle or foot (not shown). Various sensors can be located in any number of locations of the POD 10.

It is to be understood that although the POD 10 described above has been given as an example of the motorized POD, the EMG systems, devise and methods may be similarly used with other motorized prostheses or orthoses having general characteristics similar to that of the POD 10.

FIG. 1B is a perspective view of an embodiment of a POD 100 shown as a lower-limb POD having an ankle and foot unit 104 with an attachment member 102 that may be controlled with the various EMG systems described herein. The POD 100 or one or more portions thereof may be controlled with EMG based systems as described herein. The POD 100 may be used with the various EMG devices, systems and methods described herein. The POD 100 comprises an attachment member 102, which may be the lower limb member as shown in FIG. 1A, operatively coupled to a foot unit 104. As used herein, the term "attachment member" is a broad term and is used in its ordinary sense and in a prosthetic foot embodiment relates to, without limitation, any member that attaches either directly or indirectly to the foot unit 104 and is moveable in relation thereto, for example by a pivoting motion, and is used to attach the POD 100 to a stump or intermediate prosthesis. As illustrated, the attachment member 102 may take the form of a lower limb member in an ankle-prosthesis embodiment. In other embodiments, for example an orthotic embodiment, the attachment member 102 may be used to attach to and support a body part, such as with a brace, which also is moveably connected to a second member, such as a foot unit, which would also attach to and support a body part, such as the foot. In one embodiment, the attachment member 102 is a generally elongated member with a main longitudinal axis that extends in approximately a tibial direction, that is, a direction that extends generally along the axis of a natural tibia bone. For example, FIG. 1B depicts the attachment member 102 as a lower limb member in a generally vertical orientation.

In another embodiment, the attachment member 102 may comprise multiple sections. For example, the attachment member 102 may comprise two elongated sections that extend approximately parallel in a tibial direction and that are connected together. In another embodiment, the attachment member 102 comprises a two-sided chamber having two substantially symmetrical parts to form a partially enclosed housing. In another embodiment, the attachment member 102 may comprise a hollow member, such as a tube-like structure. In other embodiments, the attachment member 102 may comprise elongated flat portions or rounded portions. In yet other embodiments, the structure of the attachment member 102 is not elongated. For example, the attachment member 102 may comprise a generally circular, cylindrical, half-circular, dome-shaped, oval or rectangular structure. One example of a possible attachment member 102 embodied as a lower limb member is the ankle module and the structures described in U.S. patent application Ser. No. 10/742,455, filed Dec. 18, 2003, and entitled "PROSTHETIC FOOT WITH ROCKER MEMBER," the entirety of which is hereby incorporated herein by reference for all purposes and is to be considered as part of this specification.

In one embodiment, the attachment member 102 is generally formed of a machined metal, such as aluminum, or a carbon fiber material. In some embodiments, the attachment member 102 may comprise other materials that are suitable for prosthetic devices.

In one embodiment, the POD 100 is configured such that the main longitudinal axis of the attachment member 102 is substantially perpendicular to a lower surface of the foot unit 104 when the POD 100 is in a resting position. In another embodiment, the attachment member 102 may be substantially perpendicular to a level ground surface when the foot unit 104 rests on the ground. Such a configuration advantageously provides a user with increased support and/or stability.

As depicted in FIG. 1B, the attachment member 102 further comprises a cover 106. The cover 106 houses and/or protects the inner components of the attachment member 102. In another embodiment, the cover 106 may be rounded or may be shaped in the form of a natural human leg.

The attachment member 102 further comprises an attachment portion 108 to facilitate coupling of the attachment member 102. For example, as depicted in FIG. 1B, the attachment portion 108 of the attachment member 102 couples the POD 100 to a pylon 110. In other embodiments, the attachment portion 108 may be configured to couple the POD 100 to a stump of an amputee or to another prosthetic device, such as the POD 10 shown in FIG. 1A. Thus, in some embodiments, the POD may be an assembly of an "upper" lower-limb POD, such as the POD 10, and a "lower" lower-limb POD, such as the POD 100. FIG. 1B also depicts a control wire 112 usable to provide power to and/or communicate control signals to the POD 100.

The foot unit 104 of the POD 100 may comprise various types of prosthetic or orthotic feet. As illustrated in FIG. 1B, the foot unit 104 incorporates a design described in U.S. Pat. No. 8,007,544, issued Aug. 30, 2011, and entitled "LOW PROFILE PROSTHETIC FOOT," the entirety of which is hereby incorporated by reference and is to be considered as part of this specification. For example, the foot unit 104 may comprise a standard LP VARI-FLEX® unit available from Össur (Reykjavik, Iceland).

In one embodiment, the foot unit 104 is configured to exert a proportional response to weight or impact levels on the foot unit 104. In addition, the foot unit 104 may comprise shock absorption for comfortable loading of the heel and/or for returning expended energy. The foot unit 104 may comprise a full-length toe lever with enhanced flexibility so as to provide a stride length for the prosthetic limb that mimics the stride length of the healthy limb. In addition, as depicted in FIG. 1B, the foot unit 104 may comprise a split-toe configuration, which facilitates movement on uneven terrain. The foot unit 104 may also include a cosmesis or a foot cover such as, for example, a standard Flex-Foot cover available from Össur (Reykjavik, Iceland).

FIG. 2 is a perspective view of an embodiment of a POD 200 shown as a lower-limb POD having a knee and shank component 210 coupled with an ankle and foot component 220 that may be controlled with the various EMG systems described herein. The POD 200 or one or more portions thereof may be controlled with EMG based systems as described herein. The POD 200 may be used with the various EMG devices, systems and methods described herein. Thus, the PODs that may be used with EMG may have both knee and ankle portions. In some embodiments, the POD 10 shown in FIG. 1A may be the knee and shank component 210 of the POD 200. In some embodiments, the POD 100 shown in FIG. 1B may be the ankle and foot component 220 of the POD 200.

These are just some features of some of the example PODs that may be used with the EMG control features described herein. Other embodiments may also include a lower limb prosthesis comprising any combination of one or more joints including, without limitation, hip, knee, ankle, phalange, and/or metatarsal joints. Still other PODs, such as upper extremity for example an arm and/or hand, or other PODs, may be used with the EMG features described herein.

Figure 3:
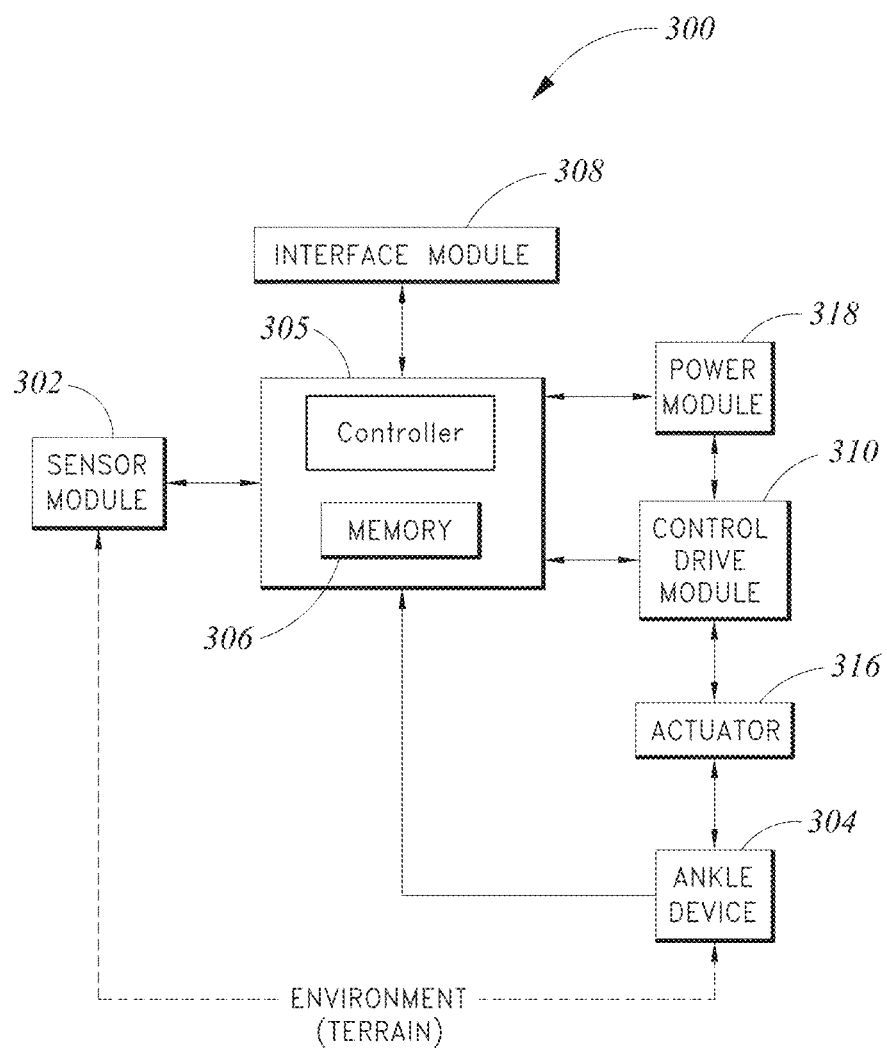
FIG. 3 is a schematic of an embodiment of a system for using EMG with the PODs of FIGS. 1A, 1B and 2.

FIG. 3 is a schematic of an embodiment of a control system 300 for using EMG with a POD. The control system 300 may have the same or similar features and/or functionalities as the control systems, or portions thereof, described for example in U.S. Pat. No. 7,811,334, issued on Oct. 12, 2010, and entitled "SYSTEMS AND METHODS AND METHODS FOR PROCESSING LIMB MOTION," and/or described for example in U.S. patent application Ser. No. 14/206,956, filed Mar. 12, 2014, and entitled "PROSTHETIC ANKLE AND METHOD OF CONTROLLING SAME BASED ON ADAPTATION TO SPEED," the entirety of each of which is hereby incorporated herein by reference for all purposes and is to be considered as part of this specification.

The prosthetic ankle device 100 can include the control system 300 to control operation of an actuator in a POD based on EMG sensors. In addition or alternatively, other devices besides ankle devices may be controlled, such as knee devices, and/or other joints. In some embodiments, the prosthetic ankle 100, and a knee used in combination with the ankle 100, can be controlled by a single control system 300. The control system 300 can include one or more of any or all of the following: a sensor module 302; the prosthetic ankle device 100; a central processing unit ("CPU") or controller 305; a memory 306; an interface module 308; a control drive module 310; actuator 116; and a power module 318. The control system 300 may include other components as well. The control system 300 may be part of the POD. Portions of the control system 300 may be part of the POD and other portions of the control system 300 may be separate from the POD. In some embodiments, the control system is distributed. For example, the sensor module 302 may include EMG sensors implanted under the skin, in the muscle, etc. that communicate wirelessly with the remaining portions of the control system 300, such as with the interface module 308. In some embodiments, the EMG sensors of the sensor module 302 are embedded in one or more muscles and the actuator 116 is an ankle actuator, as described herein, which may be used, for example, to control the neutral angle of an ankle actuator.

The control system 300 processes with the controller 305 the EMG data received from the sensor module 302. Examples of EMG data that may be received and processed are described herein, for example with respect to FIGS. 6-8 and 10. The controller 305 communicates with the control drive module 310 to control operation of the actuator 116. The CPU 305 can also receive commands from a user and/or other device through the interface module 308. FIG. 3 shows the interaction of the sensor module 302 (e.g., having a sensor used for EMG measurements), the controller 305, and an actuatable ankle device 304. Sensor module 302, which can be any sensor module described in this disclosure, can be in communication with the controller 305 and/or the interface module 308. The sensor module 302 may be in wireless communication with the controller 305 and/or the interface module 308. For example, the sensor module 302 may be an EMG sensor that is separate from the POD and communicates wirelessly with the other portions of the control system 300 of the POD. The controller 305 can comprise memory 306. As used herein, a controller can be implemented using a processor, microprocessor, application-specific integrated circuit ("ASIC"), programmable logic devices ("PLD"), field-programmable gate arrays ("FPGA"), etc. Memory 306 can include both read-only memory ("ROM") and random access memory ("RAM"), and can provide instructions and data to controller 305. A portion of memory 306 can include non-volatile random access memory ("NVRAM"). Controller 305 typically performs logical and arithmetic operations based on program instructions stored within memory 306, which may be a working memory.

Instructions in memory 306 can be executable to implement the methods described herein. Controller 305 can be in active communication with power module 318 and control drive module 310. Power module 318 and control drive module 310 can be used to power and control, respectively, actuator 316. Actuator 316 can then move ankle device 304, including, for example and without limitation, actuating a joint of ankle device 304. The information sensed by sensor module 302 can include information dependent on the terrain, as well as EMG and other measurements (e.g., any measurement described herein or elsewhere).

The system 300 contains one or more sensors in, for example in communication with, the sensor module 302, as further described herein. For example, the system 300 can include EMG sensors, nerve based sensors, osseointegrated sensors, myoacoustical signals, surface mechanomyogram (MMG), Topographic force mapping (TFM), other types of muscle or physiological sensors, inertial sensors, gyroscopes, accelerometers, magnetometers, etc. The system 300 further contains at least one actuator 316 that is electronically adjustable and capable of either providing resistance and/or actively moving the joint (e.g., using a motor). Secondary feedback signals from the actuator 316 itself may also be used as sensory information controlling subsequent actuator activity. Other joints can be mechanical and/or without actuators. The system can also include other sensors such as, without limitation, ground force sensors, angular position sensors, and joint moment sensor. The system can implement a control scheme where the control and/or behavior of the actuators can be based on, at least in part, the readings from one or more of any of the sensors described herein.

In some embodiments, the POD, such as the ankle device 304 or other PODS described herein, can use EMG signals to control the POD's actuation. EMG can include techniques for evaluating and recording the electrical activity of muscles, including, but not limited to, skeletal muscles. In some cases, the electrical signals can take the form of myoelectric signals. The myoelectric signals can vary due to muscle activity including, for example and without limitation, muscle activation and contraction. The electrical signals can also include motor action potential, muscle potential, M-waves, and/or any electrical signal (and/or electrical impulse) associated with a muscle. As used herein, an EMG signal can include any signal associated with EMG, including, for example and without limitation, measurements of any of the aforementioned electrical signals over time. EMG signals can also include any signal derived from the aforementioned signals, such as, without limitation, a signal that is a function of the electrical signals, wherein the function performs operations such as integration, addition, multiplication, division, subtraction, rectification, upscaling, downscaling, derivation, time-scaling, convolution, and/or any mathematical operation or signal processing.

The EMG signal can be created utilizing a variety of devices and/or sensors used to measure the electrical signals of the muscle. For example, and without limitation, an electromyogram can be used to generate an EMG signal. In some cases, surface EMG can record the electrical signals measured at the surface of a tissue proximate to a muscle. Typically, such measurements can involve using sensors comprising electrodes positioned on the surface of the skin. Intramuscular EMG can record the electrical signals at depths below the surface of the skin, in the muscle. Typically, sensors comprising electrodes can be implanted into the muscle for such measurements. Systems and methods of this disclosure can be used to measure electrical activity of any number of muscles, including muscles of the leg, arm, back, and/or any part of the body. A muscle can also be implanted/transplanted into the body, and the EMG signal of the implanted muscle monitored and used for any system or method described in this disclosure. Devices and/or sensors used to measure the electrical activity of those muscles can be placed in a position associated with the muscle, or a signal channel associated with that muscle. Further details of the various configurations and locations of the various sensors are described herein, for example with respect to FIG. 8.

Figure 4:
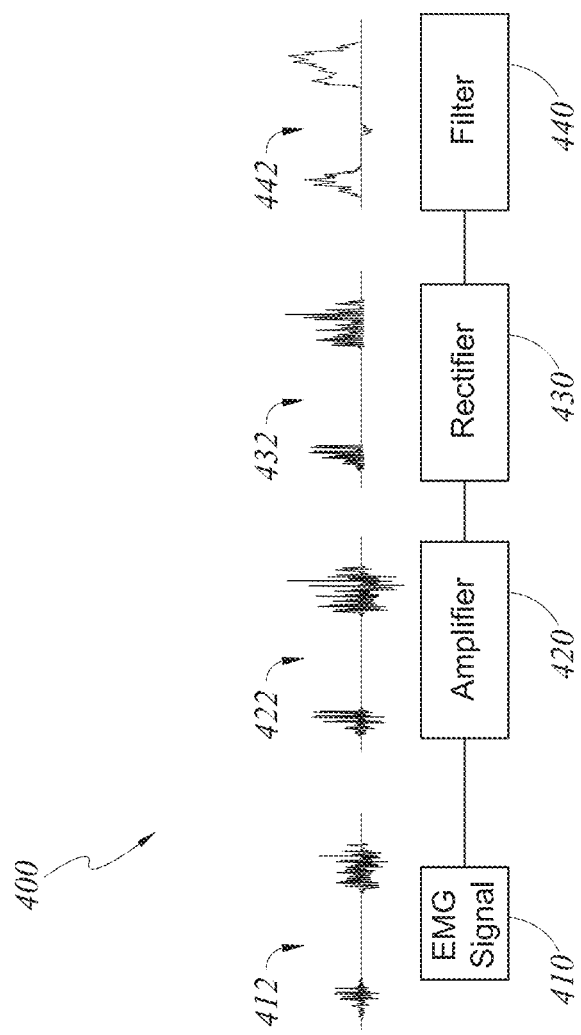
FIG. 4 is a schematic illustrating an embodiment of an EMG analysis system including an amplifier, rectifier, and filter to process an electrical signal of a muscle received with the EMG system of FIG. 3.

The sensors can include circuitry that processes an electrical signal of a muscle. For example, FIG. 4 illustrates a schematic of a system 400 including an amplifier 420, a rectifier 430, and a filter 440 to process the EMG signal 410. Such signal processing system 400 can be analyze the signal 410 using hardware and/or software. The corresponding output from the detected EMG signal 410, the amplifier 420, the rectifier 430 and the filter 440 is indicated, respectively, in the corresponding data charts 412, 422, 432, 442. The system 400 that amplifies, rectifies, and filters (for example using low-pass filters) the EMG signal 410, as illustrated in FIG. 4, can extract a linear envelope showing the approximate shape of an EMG signal measured from a muscle. For instance, a particular envelope may result from a set of EMG data. The shape and/or dimensions of such envelope may be used to control the POD. In some embodiments, the height and/or width of a rectangular envelope may be used to control the POD. For example, a muscle may be contracted a given amount, which may affect the height of the envelope. For example, a muscle may be contracted for a period of time or a number of times over that period, which may affect the width of the envelope. These are just some examples, and other stimuli can affect the envelope in a number of ways. The processing can occur at the sensors, such as those associated with the sensor module 302, and/or at a controller, such as the controller 305, in communication with the sensors. In some cases, such processing can be desirable to simplify further processing, remove noise, and/or improve signal integrity.

Other measurements can also be taken with and/or in conjunction with the EMG measurements with the EMG-related sensors and/or other type sensors, such as those that may be included in the sensor module 302. For example, and without limitation, measurements of electrical signals associated with nerves, including nerve conduction, nerve potential, neurological signals, nerve action potential, etc., can also be taken. Similarly, other physical parameters, such as temperature, blood pressure, oxygenation, blood flow, can also be measured by sensors. Sensors can also measure characteristics of motion of the user and/or POD, such as acceleration, inertia, velocity, angle, etc. Sensors can also measure position and orientation of the POD, such as displacement or angle relative to ground, joint angle, and the like. Such sensors can comprise any one or any combination of inertial sensors, gyroscopes, accelerometers, angle sensors, magnetometers, etc. A plurality of any of the aforementioned sensors can be in a singular housing/casing or in multiple housing/casings.

Any of the aforementioned measurements (e.g., EMG and/or other measurements) can be recorded over time. Such recordation can be controlled, for example, by the controller 305 using the sensor module 302. For example, and without limitation, devices and/or sensors used to measure signals can be either analog or digital. In some cases, the devices and/or sensors can measure the signals periodically in predefined time intervals, such as, without limitation, intervals of 30 seconds, 10 seconds, 1 second, 0.1 second, 0.01 second, 0.001 second, or any other interval of time as desired. A person having ordinary skill in the art should appreciate that the predefined time intervals can be set as desired. For example, the predetermined time intervals can be set such that the period is shorter than a muscle contraction so that the sensor does not miss measurements of the contraction. The devices and/or sensors can also measure the signals in a certain window of time. The window of time can begin in response to a user event, a muscular event, a bodily event, a set time, an interrogative command, a signal from a prosthetic, and/or any event desirable to read measurements by the sensors. Similarly, the window of time can end in response to a user event, a muscular event, a bodily event, a set time, an interrogative command, a signal from a prosthetic, and/or any event desirable to deactivate the sensors. By way of illustrative example, and without limitation, a POD can detect the transition from the POD being in a stance phase to the POD being in a swing phase. This transition can begin the window of time in which the devices and/or sensors measure, for example and without limitation, an EMG signal. The window of time can close when the POD detects the end of the swing phase.

In some embodiments, the window of time for reading an EMG signal can begin based at least in part on measurements taken by other sensors communicatively coupled to the POD. Such windows of time can be opened, closed, or otherwise controlled, for example, by the controller 305 using the sensor module 302. For example, and without limitation, a controller can receive signals from other sensors such as accelerometers, gyroscopes, and/or magnetometers. A change in the readings from the accelerometer, gyroscope, and/or magnetometer, such as a change that satisfies a threshold change or a rate-of-change threshold, can open the window of time. Such a change in readings can be associated with a movement of the POD, such as a toe-off and/or the beginning of a swing phase. In some embodiments, a pressure sensor can be used to measure toe-off and trigger the controller to open the window of time (for example, toe-off can be detected when pressure data from one or more pressure sensors satisfies one or more pressure thresholds). The window of time can also open in response to other events as desired. For example, and without limitation, a controller can open the window of time to receive an EMG signal once the controller finds the POD's angular velocity satisfies a velocity threshold (for example, is equal to or less than the velocity threshold, or greater than the velocity threshold), the POD's angular acceleration satisfies an acceleration threshold (for example, is equal to or less than the angular acceleration threshold, or greater than the angular acceleration threshold), and/or the POD's angle satisfies an angle threshold (for example, is equal to or less than the angle threshold, or greater than the angle threshold).

Similarly, the window of time for receiving an EMG signal can close in response to other sensors communicatively coupled to the POD. For example and without limitation, a change in the readings from the accelerometer, gyroscope, and/or magnetometer, such as a change that satisfies a threshold change or a rate-of-change threshold, can close the window of time. Such a change can be associated with changes in movement of the POD, a sudden stop in POD movement, a change in direction, a heel-on event, and/or the end of a swing phase. The window of time to receive an EMG signal can also close in response to other events as desired. For example, and without limitation, a controller can close the window of time once the controller finds the POD's angular velocity satisfies a velocity threshold (for example, is equal to or less than the velocity threshold, or greater than the velocity threshold), the POD's angular acceleration satisfies an acceleration threshold (for example, is equal to or less than the acceleration threshold, or greater than the acceleration threshold), and/or the POD's angle satisfies an angle threshold (for example, is equal to or less than the angle threshold, or greater than the angle threshold). In some embodiments, the aforementioned thresholds to close the window of time can be the same thresholds that, if satisfied, open the window of time. In certain embodiments, the thresholds can be different. For example, in some cases, the threshold(s) to open the window of time may be greater than (or less than) the threshold(s) to close the window of time. As another example, and without limitation, the window of time can close a predetermined amount of time after the window of time opens. For example, and without limitation, the window of time can close after 0.01 second, 0.1 second, 1 second, 10 seconds, or any length of time as desired. The aforementioned thresholds may, alternatively or in addition, be used to switch the power or usage of the EMG sensor between a normal and a low-power mode.

The aforementioned measurements can be transmitted (e.g., to a controller, such as the controller 305) as actual measurements taken by the sensor (e.g. included in the sensor module 302) and/or as signals derived from measurements taken by the sensor. For example, a sensor can process measurements taken by the sensor using signal processing, mathematical functions, logic, and/or an interpretation of actual measurements to produce an information signal to be transmitted. For example, and without limitation, the measurements can be input into a function that performs operations such as integration, addition, multiplication, division, subtraction, rectification, upscaling, downscaling, derivation, time-scaling, convolution, and/or any mathematical operation or signal processing. Such processing can be done by a controller communicatively coupled to the sensor, such as the controller 305 communicatively coupled with the sensor module 302.

The signals, from the sensor (e.g. the sensor module 302) and/or a controller (e.g. the controller 305) communicatively coupled to the sensor, can be received by other sensors and/or controllers as well. For example, and without limitation, sensors and/or controllers of a POD associated with one limb can communicate with the sensors and/or controllers of a POD associated with another limb. Sensors and/or controllers of different portions of the POD can communicate with each other as well. For example, some sensors and/or controllers can be associated with a knee joint and some sensors and/or controllers can be associated with an ankle joint, such as the knee joint 11 of the POD 10 and/or the ankle joint of the POD 100, or as combined in the POD 200. In some embodiments, the shank component 210 of the POD 200 can have its own control system 300 (e.g. where the "ankle device 304" is substituted with a knee device) and the foot component 220 can have its own control system 300. For instance, the sensors and/or controllers of the knee joint can communicate with the sensors and/or controllers of the ankle joint. In these and other configurations, the sensors and/or controllers can be in active communication using wired and/or wireless transmission. Wired transmission can utilize cables, such as any cable with signal line(s) and ground line(s) configured to transmit data. The sensors and/or controllers can be in active communication in a variety of other suitable ways, including but not limited to fiber optic communications, monopolar communications where the return path is via the user's body, wire-pairs for "differential signaling" (where two wires are needed, but both are "signal" and there is no "ground"), etc.

Wireless communication, e.g. transmission and/or receiving, may utilize the interface module 308. Wireless communication can occur over Bluetooth (e.g., Bluetooth low energy), ZigBee, Wi-Fi, induction wireless data transmission, medical implant communication service ("MICS"), radio frequencies, near-field communication ("NFC"), global system for mobile communications ("GSM"), and/or any other form of wireless data transmission. In some cases, the POD and communicating sensor can communicate using encryption or a private/public key combination. In some cases, the sensor can have a unique ID that is synchronized with the POD. The unique ID can be stored in memory storage in the POD.

Additional processing of the measurements can be performed by the controller, such as the controller 305. For example, an EMG signal can be monitored and adjusted according to shorter and longer term changes in the signal behavior. Dynamic scaling can be used, as further described herein, where scaling is performed to maintain substantially similar user effort for actuator activation throughout usage and to compensate for external changes of the surrounding tissue.

The controller, such as the controller 305, can also have artificial intelligence ("AI") or similar pattern recognition techniques that can recognize patterns in EMG signals or be trained to recognize patterns in EMG signals, as further described herein. The AI can be trained to recognize patterns from other sensors, including accelerometers, gyroscopes and/or magnetometers that measure other characteristics of the user and/or POD, including angle of a joint, velocity, swing, etc. The AI can be trained to take into account data from multiple sources and/or multiple characteristics of a user and/or POD, including EMG signals from a sensor coupled to a muscle, in order to control the POD. Taking into account data from multiple sources can be desirable, in some cases, in order to increase the reliability of the pattern recognition, control against noise, and/or provide fail-safes or performance improvements through the consideration of more data.

The AI can be configured to recognize patterns in measurements across a variety of characteristics (e.g., EMG, velocity, acceleration, joint angle, etc.). In some embodiments, the AI's pattern recognition can be based on a plurality of those characteristics. In some embodiments, its pattern recognition can first choose a signal of a characteristic and perform pattern recognition from that signal. For example, and without limitation, the AI can choose the signal based on the signal with the largest amplitude and/or the signal with the clearest pattern.

The use of EMG, alone or in combination with other measurements, can present certain desirable features over conventional prosthetics. In some cases, conventional methods require a user to take a first action (e.g., take a first step) in order for a POD and/or device to recognize an activity. However, the use of EMG can allow a POD to identify an action earlier than the first action. For example, a controller receiving a signal based on EMG can identify an activity based on a muscle contraction before a first action takes place (e.g., a muscle contraction before a user takes a first step). Such contraction can be initiated intentionally (e.g., a trained response) by the user to cause the controller to recognize an activity, or it can be a natural result of the user's muscular response to perform the activity, as further described herein. These and other pattern recognition approaches for EMG signals are further described herein.

Actuator responses can also be proportional to characteristics of a measured EMG signal (for example, amplitude (minimum, maximum, average, etc.), frequency, response time, rate of change). In some embodiments, the controller 305 and/or control drive module 310 may operate the actuator 316 to respond proportionally to signals of the EMG sensors and/or other sensors of the sensor module 302. For example, and without limitation, an EMG signal with larger amplitudes can cause the POD to move faster or cause different and/or multiple joints of the POD to actuate. An EMG signal with high frequency can cause the POD to operate with greater stiffness levels. A person having ordinary skill in the art should appreciate that a POD could be configured to react to any characteristic of the EMG signal in a predefined way as desirable. In some cases, a user may have multiple prosthetic devices. For example and without limitation, an above-knee amputee can have both a bionic ankle and knee. The user can also have bionic hips, upper extremities, other lower extremities, etc. In some cases, these multiple prosthetic devices can be synchronized and/or coordinated with one another. For example, and without limitation, the multiple prosthetic devices can be communicatively coupled to one another to transmit/receive state information, EMG signals, signals from sensors, etc. to each other. The receiving prosthetic can then control movement of actuators based at least in part on the received information.

In some cases, the AI can receive an EMG signal and determine not to use the EMG signal. For example, and without limitation, the AI can determine that the EMG signal does not have enough signal integrity or reliability to use it for pattern recognition. By way of illustration, the AI can identify that the EMG signal, measured and/or amplified, does not exceed a predefined amplitude threshold, and is too weak to be relied upon for pattern recognition. As another example, the AI can choose not to use an EMG signal to identify certain activities due to the reliability of an EMG signal in indicating those activities. In some cases, some example reasons why an EMG signal may not be as reliable as other signals is the speed in which the activity happens, or that the activity does not require a strong enough muscle response to occur. Some examples of such activities can include toe-up during walking and fast transitions in walking speeds.

Dynamic Scaling

In some embodiments, a controller such as the controller 305 can be used for signal processing. Such signal processing can include dynamic scaling of a signal (e.g., an EMG signal and/or a signal associated with any measurement of this disclosure) to address certain changes in the signal. For example, an EMG signal can be monitored, for example by the sensor module 302 and/or the controller 305, and adjusted, for example by the controller 305, according to shorter- and longer-term changes in signal behavior. The signals can also be communicated via the interface module 308 for analysis, monitoring, etc. by a separate device or separate portion of the POD. The scaling can be performed to maintain the same user effort for actuator activation throughout a full day of usage and to compensate for physical changes in the user (e.g., changes in muscle strength). In some embodiments, dynamic scaling can also be used to account for long-term muscle system changes, short-term muscle signal changes, and changes in sensor alignment in the muscle.

Indeed, an EMG signal can vary based on muscle strength and/or other long-term characteristics of a muscle (e.g., changes in muscular tissue). For example, increased muscle growth can result in a changed EMG signal, and muscle degeneration can result in a changed EMG signal. Accordingly, an EMG signal can be monitored for long term changes in, for example and without limitation, minimum, maximum and average amplitudes of the EMG signal, a shorter or longer response time, or a larger or smaller rate of change. These long term changes can be accounted for by a controller by scaling the signal. For example, if a muscle weakens and the EMG signal becomes smaller in amplitude, a dynamic scaler can amplify the signal by a gain greater than or equal to unity gain (positive or negative), to account for the weakened signal. Similarly, a strengthened muscle with a larger signal can have the signal amplified by a gain less than or equal to unity (positive or negative) in order to decrease the amplitudes of the signal for processing.

Similarly, there can be changes in an EMG signal due to short term muscle changes. For example, and without limitation, an EMG signal can change due to user muscle fatigue. Accordingly, EMG signal properties can be monitored for short term changes in, for example and without limitation, minimum, maximum and average amplitudes of the EMG signal. In some cases, if a muscle becomes fatigued, an EMG signal measured from the muscle can have smaller amplitudes. For example, the EMG signal of a muscle can decrease slowly throughout a day as the muscle is used. A dynamic scaler can amplify the signal by a positive gain to account for the small signal of the fatigued muscle during processing.

Also, a signal can change due to changes in sensor alignment. For example, a sensor, such as in the sensor module 302, implanted in a muscle measuring the EMG signal from the muscle can move within the muscle after implantation. Similarly, a sensor placed on the surface of tissue can also move from its original position over time. These movements can be caused by drift of the sensor, or by tissue changes. Such movements can cause changes in the measured signal. If the movement is minimal, and the signal is still strong enough, the system can still use the signal, but can adjust the scaling by comparing the signal to AI gait algorithms to identify the correct levels of the scaled EMG signals. Sensor signal quality can be monitored to estimate if the sensor signal is valid by comparing the signal to patterns occurring in known gait states.

Direct Control

Muscle contractions can be used to directly control an actuator, such as the actuator 316, associated with a joint. As described above, sensors such as in the sensor module 302 can be implanted in any muscle to measure EMG signals of that muscle. As an illustrative example, and without limitation, sensors can be placed in any muscle associated with the upper leg-muscle (e.g., vastus lateralis, vastus intermedius, adductor magnus, bicepts femoris short head, bicepts femoris long head, gluteus maximus, tensor fascia lata, satorius, lliopsoas, pectineus, adductor longus, gracilis, vastus lateralis, rectus femoris, vastus medialis, gastrocnemius, tibialis anterior, etc.). Accordingly, the activation of the muscle associated with the upper-leg can be used to control the actuation of a joint in the lower leg POD of that same leg, such as the POD 100. However, it can also be desirable to control actuation of a joint of the lower leg POD using a muscle not located and/or associated with that same leg. Accordingly, another muscle can, in addition or alternatively, be trained and/or used to control actuation of a joint of the lower-leg POD. For example, and without limitation, a muscle in the arm (e.g., brachio radialis, triceps brachil, brachialis, etc.) and/or torso (e.g., trapezius, latissimus dorsi, external oblique, etc.), and/or healthy leg and/or anywhere in the body can be measured. Again, sensors can be placed in a plurality of muscles. Accordingly, a plurality of muscles can be used to control the actuation of the joint of the lower-leg POD. Further, the sensors associated with these various locations need not be the same type of EMG sensor. For example, some may be external, subcutaneous, intraperitoneal, epimysial, intramuscular, and/or other EMG sensors.

In some embodiments, the EMG signal of the muscle can control the actuator activation of a POD. For example, the EMG signal of the muscle may be sensed by the sensor module 302 and the controller 305 may control the actuator 316 based on the detected EMG signal. For example, and without limitation, an EMG signal can be used to give a user additional and/or full control of a prosthesis actuator. In some cases, the muscle contraction would translate directly to actuator activation. Accordingly, the amplitude of the EMG signal, the frequency, the minimum/maximum, number of zero crossings, and/or other characteristics of the EMG signal can be used to control an actuator. For example, and without limitation, once the amplitude of an EMG signal exceeds a predetermined amplitude threshold and/or the frequency of the EMG signal exceeds a predetermined frequency threshold, the actuator can become activated. As another example, an EMG signal with a larger amplitude can cause an actuator to actuate more than an EMG signal with a smaller amplitude.

In some embodiments, the EMG signal can be used to control the amount of actuator activation during stance phase. For example, and without limitation, the EMG signal can be used to control an actuator to output the desired amount of flexion during stance phase. The EMG signal can also be used to control an actuator to output the desired amount of resistance during a stance extension state.

In some embodiments, the EMG signal can be used to control the actuator activation during sitting down phase. For example, and without limitation, the actuators of a POD can use an EMG signal to control the speed of the POD as the user moves to a seated position.

In some embodiments, the EMG signal can be used to control the actuator activation during stair descent and/or stair ascent. For example, and without limitation, the actuators, such as the actuator 316, of a POD, such as the POD 10, 100 or 200, can control the resistance during initial bending and/or during the rest of the ascent or descent phase. In some cases, the actuators can control the resistance during initial bending and during the rest of the ascent or descent phase independently.

In some embodiments, the EMG signal can be used to control target swing extension angle. For example, and without limitation, a user can have a self-selected knee angle position following heel strike. The POD can use the EMG signal to detect the heel strike, and then actuate the knee to the self-selected knee angle position.

Mode Selection

A user can send certain EMG signals to the POD by contracting one or more muscles in a certain pattern to enable certain usage modes. EMG signals can be measured at surface and/or implanted sensors, or any other EMG sensors described herein such as subcutaneous etc., for example with the sensor module 302. The EMG signaling can be used to select certain gait phases or certain conditions of the POD. For example, and without limitation, the certain patterns can include contracting a muscle a predetermined number of times in a period of time, contracting a muscle for a predetermined length of time and/or intensity, contracting muscles in a certain sequence, and/or clicking a muscle. A click can include activating one or more muscles for a certain amount of time. By way of illustration, if the user contracted his thigh muscle 3 times in a 2 second time interval, a controller of the POD could recognize those contractions as signaling that the user intends to put the POD in stair ascent mode. Accordingly, the POD could place itself into stair ascent mode.

As another example, the user could contract a muscle for a certain amount of time to place the POD in a certain mode. By way of illustration, if the user held a thigh contraction for 3 seconds, a controller, such as the controller 305, of the POD could recognize this contraction as signaling that the user intends to put the POD in a stair descent mode. Accordingly, the POD could place itself into stair descent mode.

A person having ordinary skill in the art should appreciate that there can be any number of muscle patterns from single or combinations of two or more muscles that a POD could be trained to recognized. A user can train the POD to recognize such patterns as desired. Accordingly, the precise patterns used to set the POD into particular mode can vary between users and can depend on user preferences. For example, and without limitation, a controller of the POD could recognize EMG signals indicative of muscle contractions of predetermined lengths, frequency, intensities, and/or any combination of those characteristics.

Moreover, the POD can use the aforementioned EMG signal patterns to place the POD into a number of different modes. For example, the sensor module 302 may detect the muscle behavior and communicate signals related to the behavior to the controller 305 for appropriate control of the actuator 316. In some embodiments, a user can send certain EMG signals to select a stair ascent mode. For example, and without limitation, a user can send a certain EMG signal to the POD that there are upcoming stairs and the user intends to use stair ascension mode for ascending the stairs. In such a case, the pattern of contraction by the user can be identified by the POD. The POD can then prepare for the stairs before the sensor system is able to identify (e.g., using involuntary control as will later be described) the new terrain the user is entering.

In some embodiments, a user can send certain EMG signals to select a stair descent mode. For example, and without limitation, a user can signal the POD that there are upcoming stairs and that the user intends to use stair descent mode for descending the stairs. The POD can then prepare for the stairs before the sensor system is able to identify the new terrain (e.g., using involuntary control as will later be described) the user is entering.

In some embodiments, a user can send certain EMG signals to select a ramp ascent mode. For example, and without limitation, a user can signal the POD that there is an upcoming ramp and that the user intends to use ramp ascension mode for ascending the ramp. The POD can then prepare for the ramp before the sensor system is able to identify the new terrain (e.g., using involuntary control as will later be described) the user in entering.

In some embodiments, a user can send certain EMG signals to select a ramp descent mode. For example, and without limitation, a user can signal the POD that there is an upcoming ramp and that the user intends to use ramp descent mode for descending the ramp. The POD can then prepare for the ramp before the sensor system is able to identify the new terrain (e.g., using involuntary control as will later be described) the user in entering.

There can be any number of other modes that can be pre-defined or defined by the user for the user to select by sending certain EMG signals. A person having ordinary skill in the art should appreciate that this can include a great variety of activities, including any activity that a user can partake. For example, and without limitation, a user can signal the device that the user is going to perform certain activity that has already been programmed into the prosthetic device, e.g. golfing, biking, Nordic walking etc. Then the prosthetic device can improve the control functions to work for those activities without implementing the control functions in the normal mode of the prosthesis. Further, these and other modes, as well as the manner of entering and exiting the modes, may be customized for a particular user of the POD.

In some cases, these modes can also be selected by pushing a button associated with the POD, or selecting the mode on a user interface, such as the interface module 308, communicatively coupled to the POD. The button or user interface can be used to select an activity prior to performing the activity in order to configure the POD to perform that activity. The button and/or user interface can be used alone and/or in combination with any system or method described in this disclosure. In some embodiments, the button and/or user interface can be used in combination with surface/external, subcutaneous, intraperitoneal, epimysial and/or intramuscular EMG sensor signals.

Involuntary Control

Figure 5:
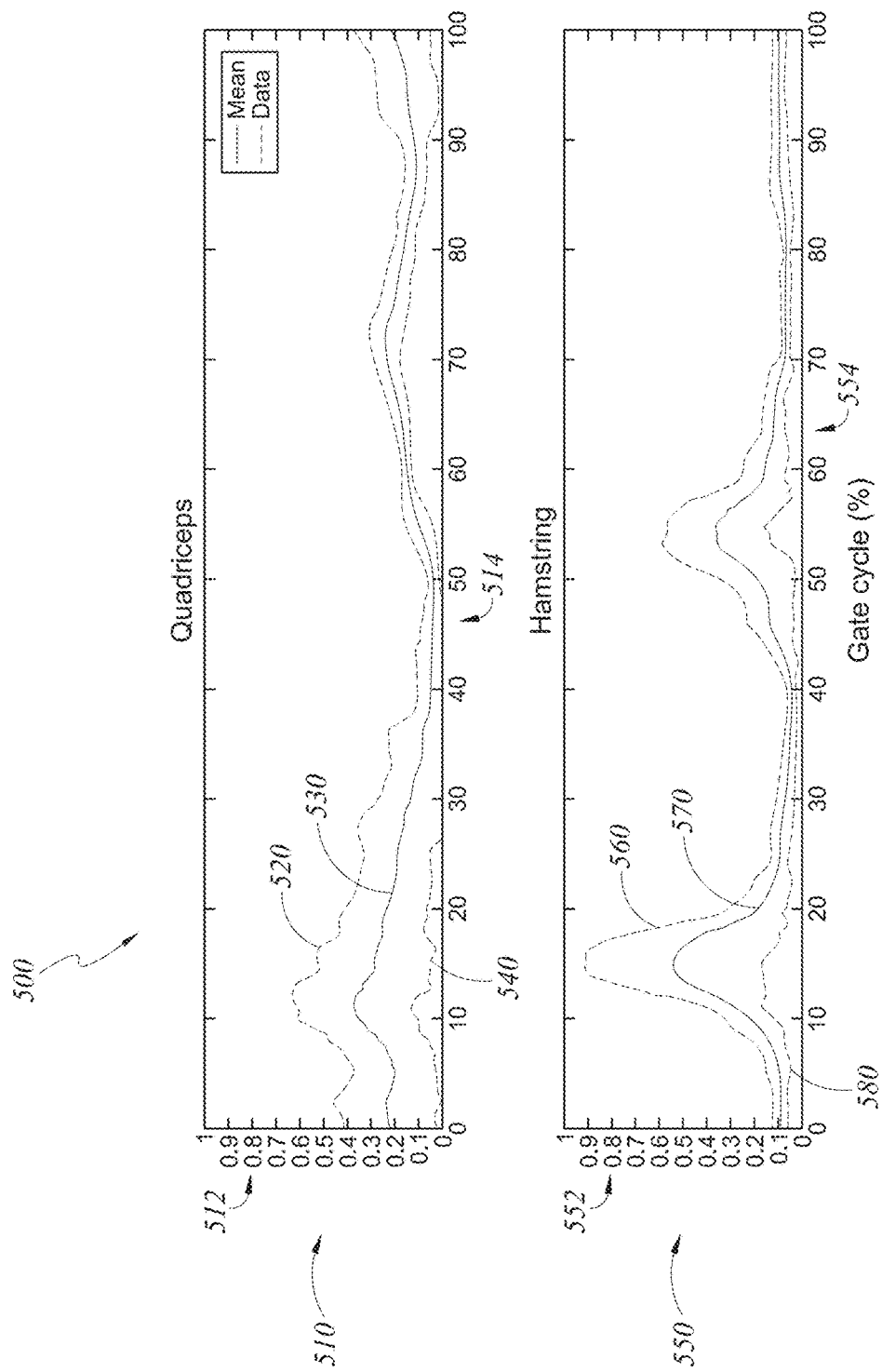
FIG. 5 is a graph illustrating embodiments of EMG data for quadriceps and hamstring muscles during level ground walking that can be used by the various control systems herein to control the various PODs described herein.
Figure 6:
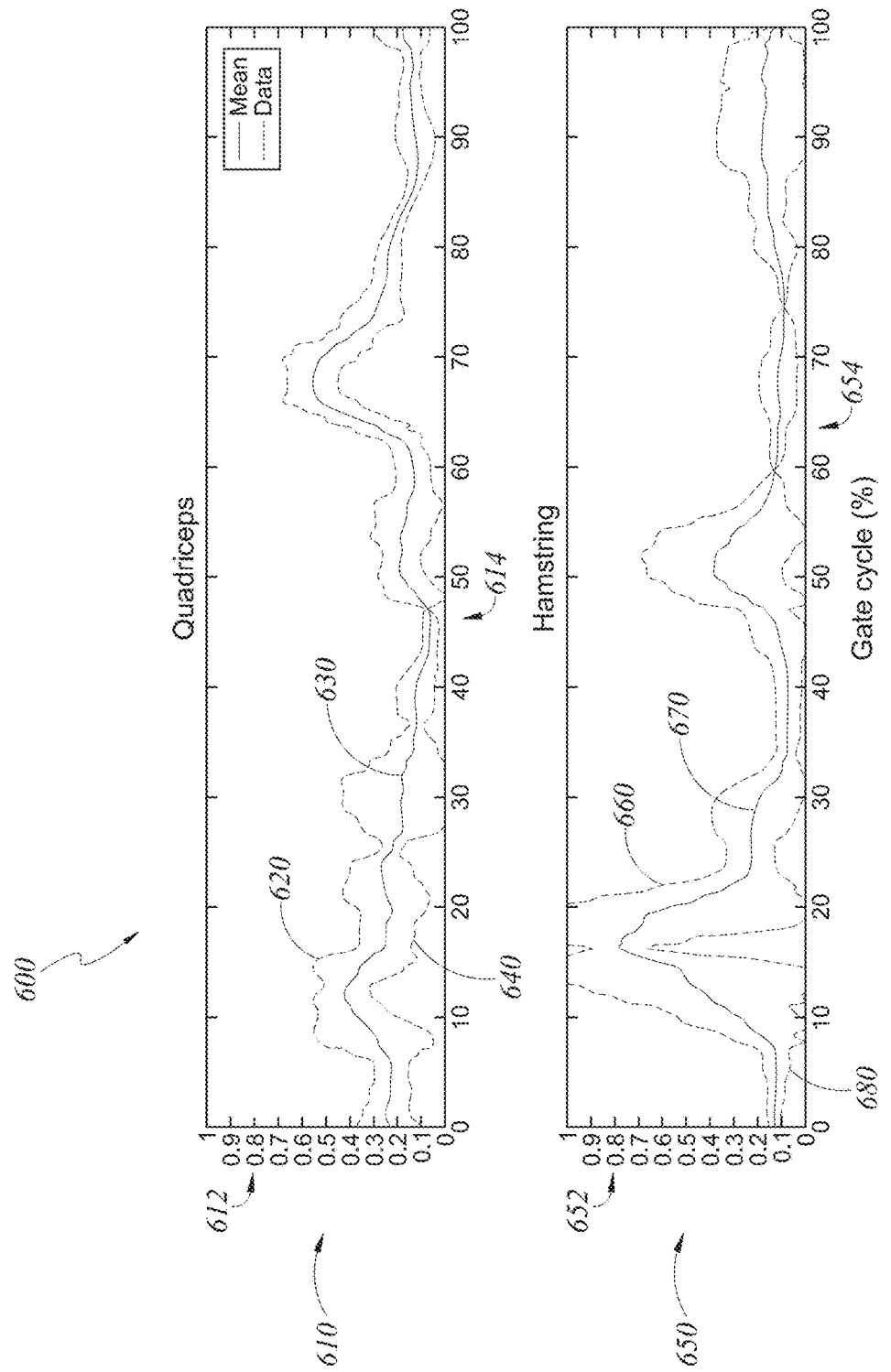
FIG. 6 is a graph illustrating embodiments of EMG data for quadriceps and hamstring muscles during ramp descent that can be used by the various control systems herein to control the various PODs described herein.
Figure 7:
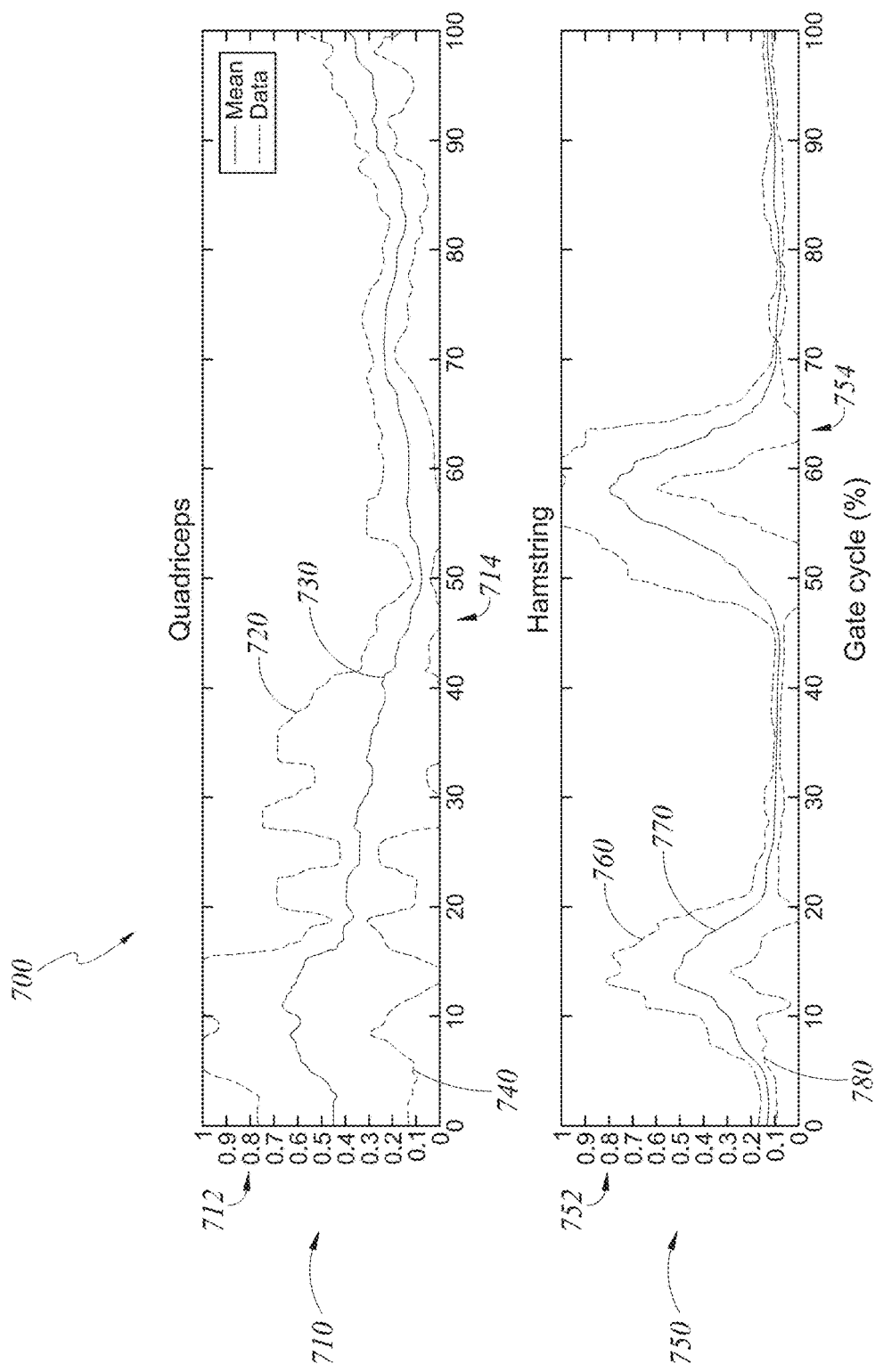
FIG. 7 is a graph illustrating embodiments of EMG data for quadriceps and hamstring muscles during ramp ascent that can be used by the various control systems herein to control the various PODs described herein.

In some embodiments, EMG signals can be monitored during regular gait, and certain gait events can be identified based at least in part on EMG signal patterns received during the gait event. For example, the sensor module 302 may detect EMG signals and the controller 305 may identify a gait event based on the detected EMG signals during the event. Also, different actions can be monitored and identified based at least in part on EMG signals. These actions can include ramp ascent, ramp descent, shaking, stance, jogging, running, walking, and/or any other action that a user can take using a POD. FIGS. 5-7 are graphs illustrating embodiments of data collection and analysis of EMG signals for quadriceps and hamstring muscles during, respectively, level ground walking, ramp descent and ramp ascent. These EMG signals and patterns can be used for actuator activation. For example, the sensor module 302 may detect EMG signals and the controller 305 may identify and/or monitor these and other actions based on the detected EMG signals to actuate the actuator 316.

As shown in FIG. 5, the EMG data 500 for level ground walking includes a first graph 510 and second graph 550 showing EMG signal activity during level ground walking for, respectively, the quadriceps and the hamstring. The first graph 510 depicts a vertical axis 512 with a measure of EMG activity of the quadriceps during level ground walking and a horizontal axis 514 indicating percentage of the level ground walking gait cycle. The mean of the collected data is shown as line 530 with the standard deviation indicated by the lines 520 and 540. The second graph 550 depicts a vertical axis 552 with a measure of EMG activity of the hamstring during level ground walking and a horizontal axis 554 indicating percentage of the level ground walking gait cycle. The mean of the collected data is shown as line 570 with the standard deviation indicated by the lines 560 and 580.

As shown in FIG. 6, the EMG data 600 for ramp descent includes a first graph 610 and second graph 650 showing EMG signal activity during ramp descent for, respectively, the quadriceps and the hamstring. The first graph 610 depicts a vertical axis 612 with a measure of EMG activity of the quadriceps during ramp descent and a horizontal axis 614 indicating percentage of the ramp descent gait cycle. The mean of the collected data is shown as line 630 with the standard deviation indicated by the lines 620 and 640. The second graph 650 depicts a vertical axis 652 with a measure of EMG activity of the hamstring during ramp descent and a horizontal axis 654 indicating percentage of the ramp descent gait cycle. The mean of the collected data is shown as line 670 with the standard deviation indicated by the lines 660 and 680.

As shown in FIG. 7, the EMG data 700 for ramp ascent includes a first graph 710 and second graph 750 showing EMG signal activity during ramp ascent for, respectively, the quadriceps and the hamstring. The first graph 710 depicts a vertical axis 712 with a measure of EMG activity of the quadriceps during ramp ascent and a horizontal axis 714 indicating percentage of the ramp ascent gait cycle. The mean of the collected data is shown as line 730 with the standard deviation indicated by the lines 720 and 740. The second graph 750 depicts a vertical axis 752 with a measure of EMG activity of the hamstring during ramp ascent and a horizontal axis 754 indicating percentage of the ramp ascent gait cycle. The mean of the collected data is shown as line 770 with the standard deviation indicated by the lines 760 and 780.

In some embodiments, the pattern of the EMG signals can be used to detect a stance-to-swing transition. A swing phase usually starts at approximately 60% of a complete gait cycle. As shown in FIGS. 5-7, between approximately 40-50% of the gait cycle, an increased activity can be seen in the hamstring muscle for level ground walking (FIG. 5), ramp descent (FIG. 6) and ramp ascent (FIG. 7). A controller can be configured to identify such a pattern in a received EMG signal in order to determine a user's intention to transition from stance phase to swing phase. For example, and without limitation, the controller, such as the controller 305, can be configured to analyze characteristic of the EMG signal, such as the average EMG signal amplitude in a window of data, a time series analysis, the frequency of an EMG signal, and/or maximum/minimum. The controller could also monitor if the amplitude of the EMG signal exceeded a predefined amplitude threshold. The controller could also monitor the slope of the EMG signal and compare the slope to a predefined slope threshold. For example and without limitation, a positive slope above a predefined slope threshold could indicate to the POD that the user is entering a stair ascent. The POD could then switch to a stair ascent mode.

The POD can also store in memory, such as the memory 306, example EMG signal patterns that correspond to known transitions. The known transitions may be customized EMG signal patterns for a particular user. These EMG signal patterns can be stored in a dynamic library that can be updated as desired. The controller of the POD can then run correlation algorithms and/or comparisons between the stored EMG signal patterns and the measured EMG patterns. For example, and without limitation, the controller can compare the stored EMG signal to measured EMG signal using characteristics such as frequency, amplitude, zero-crossings, derivations, integrals, and/or any signal characteristic known in the art. If the measured EMG signal substantially matches a stored EMG signal pattern across those characteristics, the controller of the POD can match the measured EMG signal pattern to the transition of the stored EMG signal pattern. As mentioned, FIGS. 5-7 illustrate some of the characteristic patterns of particular muscle groups during certain gait events.

A controller can monitor EMG signals along with measurements taken by other sensors (e.g., accelerometers, inertia sensors, gyroscopes, magnetometers, pressure sensors, and/or any other sensors described in this disclosure). As described in this disclosure, certain embodiments can monitor the pattern of one or more sensors in determining actions taken by the user. For example, and without limitation, the AI of the controller can be configured to recognize patterns in measurements across a variety of characteristics (e.g., EMG, velocity, acceleration, joint angle, etc.). In some embodiments, the AI's pattern recognition can be based on a plurality of those characteristics. In some embodiments, its pattern recognition can choose a signal of a characteristic and perform pattern recognition from that signal.

Similarly, for many patients, a combination of active control, such as contracting muscles in certain patterns as described above, and involuntary control can be used. For illustrative purposes, and without limitation, a patient typically has many muscle contractions associated with knee movement. For example, a user who would like to move a knee joint can naturally have muscular contractions in the hamstrings and quadriceps. As a result, monitoring patterns in the hamstrings and/or quadriceps can be effective at providing involuntary control of a prosthetic knee joint. However, in some cases, the muscles that would naturally contract to control a joint may have been amputated. For example, the muscles that control lower-leg movements in a transfemoral amputee may have been amputated. In such cases, active control can be more effective at providing control of the lower-leg prosthetic joints than involuntary control based at least in part on natural muscle contraction. In some cases, a combination of active and involuntary control can be used. For example and without limitation, some of the muscles that control a joint may be damaged or altered. As a result, their contraction patterns can provide some information on user activity, but the patterns do not distinctly identify the activity. In such cases, the user can also use some active control for that activity so that the AI of the POD recognizes a behavior when the user actively contracts a muscle in a certain pattern and the user involuntarily contracts muscles in a certain pattern. In any case, whether the POD uses active and/or involuntary control, the POD can use measurements taken by other sensors regarding other characteristics, as described in this disclosure, along with the EMG signal.

Control of Gait State Transition in MPK Knees Using EMG Information

In some embodiments, EMG data coming from antagonist muscles of the lower-limb can be used to gain information of the state of gait. Such information can be used to better manage states of a prosthetic, such as a microprocessor-controlled knee ("MPK"), and its transitions.

Control of Ankle Joint Position Based on EMG Information

In some embodiments, an ankle of the POD 100 or POD 200 may be controlled based in whole or in part on EMG signal data. The ankle may be the ankle device 304. In some embodiments, ankle prostheses from Spring Active, Inc. (Tempe, Ariz.) may be used and controlled with the EMG systems and methods described herein. The ankle device controlled with the EMG systems and methods described herein may be any of various ankle prosthetic devices, such as those described, for example, in U.S. patent application Ser. No. 13/767,945, filed Feb. 15, 2013, and entitled CONTROL SYSTEMS AND MATHODS FOR GAIT DEVICES, or in U.S. Pat. No. 9,289,316, issued Mar. 22, 2016, and entitled QUASI-ACTIVE PROSTHETIC JOINT SYSTEM, the entire disclosure of each of which is hereby incorporated by reference herein for all purposes. These are just some examples of the ankle devices that may be used with the various EMG control techniques described herein. Other suitable ankle devices may be used. The control system 300 may be used to control the ankle. The processing system 400 may be used to process the EMG signals for control of the ankle. The EMG data 500, 600 and/or 700 may be used in the control of the ankle.

Figure 8:
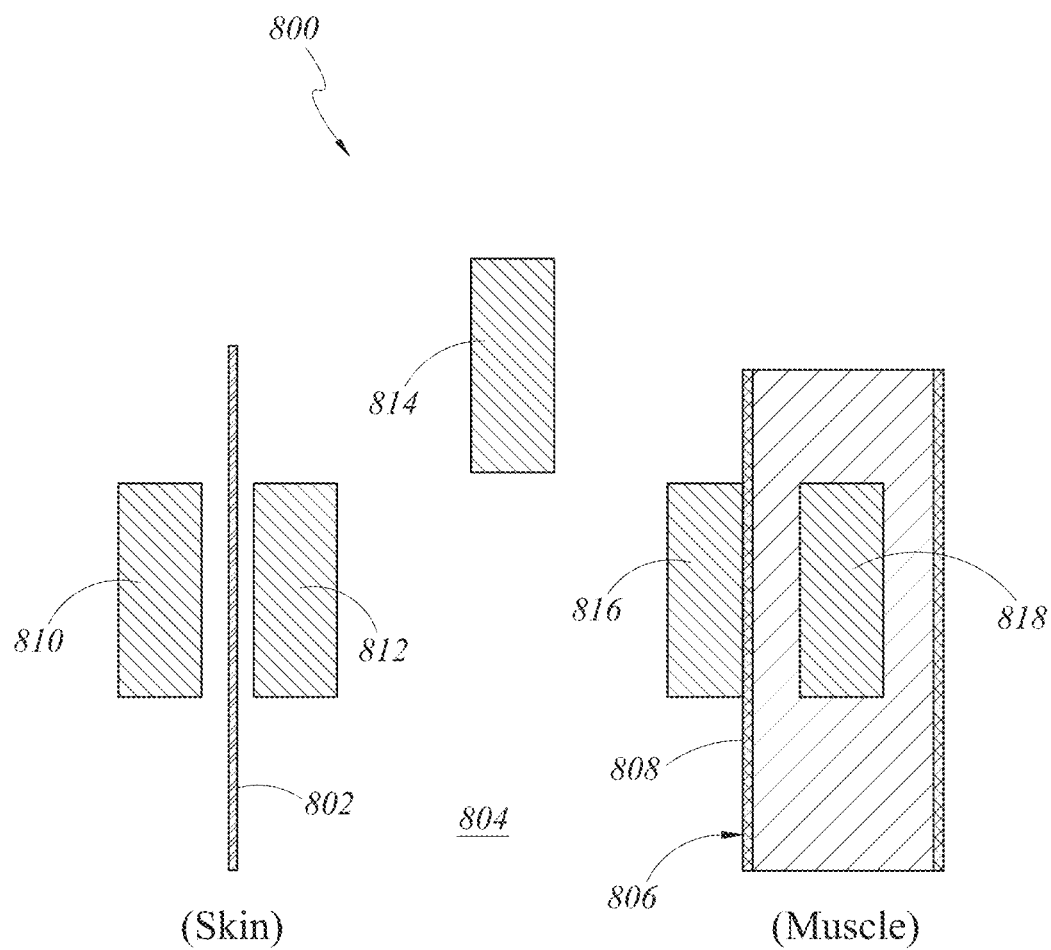
FIG. 8 is a schematic illustrating embodiments of example EMG sensor types and configurations, including external, subcutaneous, intraperitoneal, epimysial and intramuscular EMG sensors, that can be used by the various control systems herein to control the various PODs described herein.

Ankle position control based on EMG, and the other control approaches described herein (for example direct, involuntary, gait state transition, click control, impedance modulation, activity transitions, AI training, etc.) can incorporate a variety of EMG sensor types and/or a variety of EMG sensor configurations. FIG. 8 is a schematic illustrating embodiments of possible EMG sensor types and configurations that may be used with the neutral position control, or with any other EMG-based control techniques described herein.

As shown in FIG. 8, a system 800 of EMG sensors may be incorporated into the body in various locations. The skin 802 is schematically shown, where the left side of the skin 802 as oriented in FIG. 8 is external to the body and the right side of the skin 802 as oriented is internal to the body. A schematic of a muscle 806 surrounded by an epimysium 808 is thus shown inside the body. The skin 802 may be skin on any part of the body, including skin on the feet, ankles, legs, hips, torso, chest, fingers, arms, or other body parts. The muscle 806 may be any muscle of the human body, as described herein. In some embodiments, there may be multiple skin locations and/or multiple muscles used in the system 800. The system 800 of EMG sensors may include one or more external EMG sensors 810, and/or one or more subcutaneous EMG sensors 812, and/or one or more intraperitoneal EMG sensors 814, and/or one or more epimysial EMG sensors 816, and/or one or more intramuscular EMG sensors 818. Any or all of the sensors 810, 812, 814, 816, 818 may be included with or otherwise in communication with the sensor module 302 of the control system 300. By "external EMG sensor" it is understood to have its ordinary and usual meaning, and includes for example a surface EMG placed directly or indirectly on, i.e. the outward side of, the skin, such as a skin location that is above or otherwise adjacent a muscle. By "subcutaneous EMG sensor" it is understood to have its ordinary and usual meaning, and includes for example an EMG sensor placed directly or indirectly under, i.e. the inward side of, the skin, such as a location under the skin and in between the skin and a muscle. By "intraperitoneal EMG sensor" it is understood to have its ordinary and usual meaning, and includes for example an EMG sensor placed into the peritoneum or the body cavity. By "epimysial EMG sensor" it is understood to have its ordinary and usual meaning, and includes for example an EMG sensor placed directly or indirectly on the epimysium 808, which may be s sheath of fibrous elastic tissue surrounding the muscle 806.

FIGS. 9A-9C are schematics illustrating embodiments of EMG sensor and analysis systems that may be used with the various control systems and methods described herein. FIGS. 9A-9C show, respectively, a subcutaneous EMG system 900, a hub with wired EMG system 930, an and EMG with external coil system 960. As shown in FIG. 9A, the subcutaneous EMG system 900 includes a schematic of the body 902 having an internal region 904 and skin 906. The EMG sensor system 910 includes an external EMG sensor 912 and a subcutaneous EMG sensor 914. The subcutaneous EMG sensor 914 includes interfaces 916 for detecting EMG and other signals, for transmitting and receiving communications and/or for receiving power. The external EMG sensor 912 may be any of the external EMG sensors described herein, for example the external EMG sensor 810. The subcutaneous EMG sensor 914 may be any of the subcutaneous EMG sensors described herein, for example the subcutaneous EMG sensor 812. The sensor system 910 may include or be a part of the sensor module 302. The sensor system 910 may be in communication, either wired or wireless, with an interface 920. The interface 920 may have the same or similar features and/or functionalities as the interface module 308. The EMG signals detected with the sensor system 910 may be decomposed from the totality of signals collected by a decomposition module 922. The resulting EMG signals may be displayed, analyzed, etc. by the signals module 924. Modules 922 and/or 924 may be components of the controller 305. The various data may be communicated, either wired or wirelessly, between the interface 920, the decomposition module 922 and the signal module 924.

As shown in FIG. 9B, the hub with wired EMG system 930 includes a schematic of the body 932 having an internal region 904 and skin 906. The hub with wired EMG sensor system 930 includes an external EMG sensor 942 and a subcutaneous EMG sensor 944. The subcutaneous EMG sensor 944 includes a hub 944 with electrodes 948 connected to the hb 944 via wires 946. The electrodes detect EMG signals and transmit the signal along the wire 946 to the hub 944. The external EMG sensor 942 may be any of the external EMG sensors described herein, for example the external EMG sensor 810. The subcutaneous EMG sensor 948 may be any of the subcutaneous EMG sensors described herein, for example the subcutaneous EMG sensor 812. The sensor system 930 may include or be a part of the sensor module 302. The sensor system 930 may be in communication, either wired or wireless, with an interface 950. The interface 950 may have the same or similar features and/or functionalities as the interface module 308. The signals detected with the sensor system 930 may be displayed, analyzed, etc. by the signals module 954. The module 954 may be a component of the controller 305. The various data may be communicated, either wired or wirelessly, between the interface 950 and the signal module 954.

As shown in FIG. 9C, the EMG with external coil system 960 includes a schematic of the body 962 having an internal region 904 and skin 906. The EMG with external coil system 960 includes embedded or implanted EMG sensors 962, 964, 966 that detect EMG signals. A coil 970 surrounds the body 962 portion having the implanted EMG sensors 962, 964, 966. Implanted EMG sensors allow for EMG signals to be measured at their source providing relatively cross-talk-free signals that can be treated as independent control sites. An external telemetry controller, such as the coil 970, receives signal telemetry sent over a magnetic link by the implanted electrodes. The coil 970 may be external and thus the telemetry may be transmitted transcutaneously to the coil 970. The same link may provide power and/or commands to the implanted EMG sensors 962, 964, 966. Wireless telemetry of EMG signals from sensors implanted in the residual musculature may help mitigate the risk of infection, breakage, and marsupialization. Each implanted EMG sensor 962, 964, 966 may include an application-specified integrated circuit that is packaged into a bio-compatible capsule. The EMG sensors 962, 964, 966 may be designed for permanent long-term implantation with no servicing requirements. Signals from the implanted EMG sensors 962, 964, 966 in the body 962, linked through the coil 970, may control the POD via reverse telemetry. Power may be supplied to the implanted EMG sensors 962, 964, 966 through the coil 970 using forward telemetry. The sensor system 960 may be in communication, either wired or wireless, with an interface 980. As shown, the interface 980 may be in wired communication with the coil 970. The interface 980 may have the same or similar features and/or functionalities as the interface module 308. The signals detected with the sensor system 960 may be displayed, analyzed, etc. by the signals module 984. The module 984 may be a component of the controller 305. The various data may be communicated, either wired or wirelessly, between the interface 980 and the signal module 984.

The ankle or other joints can be controlled with the various EMG sensors and systems based on experimental data. The various EMG control techniques can be based, in whole or in part, on experimental data relating to muscle activity. Such data may be based on data from the general population or data specific to a particular user or to a particular type of user. As mentioned, data described herein may be used, such as the graphs of FIGS. 5-7 showing EMG data for quadriceps and hamstring muscles during various ambulating actions. Further, experiments for activation testing of various muscle groups may be used. In some embodiments, data collected from generic muscle activation tests may be used. These tests may be done to identify a particular user's, or a particular type of user's, capability of contracting an individual muscle on command. Such tests may include a subject contracting a particular muscle without performing a particular activity (such as ankle or other movements) and then measuring the resulting EMG signals. Other tests involve device specific activation testing and functional actuation testing. For instance, the device specific activation testing can include a basic activation testing (e.g. to check if the user can control the function), actuation response testing (e.g. to measure how fast the user can respond), functional actuation testing (e.g. to examine the muscle activity and control during various activities), fine control actuation testing (e.g. to measure how accurately a user can perform a function, such as dorsiflex to a predefined degree of ankle angle), and other suitable testing. Particular test results are described in further detail below. The results of such tests indicate that these particular subjects are capable of repeatedly generating EMG signals from particular muscles of sufficient quality to be used for control of a POD. The results also identify what type of control scheme would be best for that user or that particular type of user. The results showed that the signal to noise ratio from the implanted EMG sensors to be high enough to control a prosthetic function. The subjects were able to create a usable signal from each muscle with some co-contractions during initial assessment testing but improving over time. The results further showed the signal to be of consistently good quality. The co-contractions were manageable and the subjects' ability to isolate the muscle contraction seemed to improve with time. The subjects demonstrated direct control over the prosthesis during ambulatory and non-ambulatory functions.

In some embodiments, experimental results from generic muscle activation tests may be used. Experimental results from a first test, of a transtibial amputee subject, for generic activation of the tibialis anterior and corresponding measured EMG activity from an implanted EMG sensor are shown in Table 1. The tibialis anterior is a muscle mostly located near the shin that originates in the upper two-thirds of the lateral (outside) surface of the tibia and inserts into the medial cuneiform and first metatarsal bones of the foot. It acts to dorsiflex and invert the foot. Experimental results of the same transtibial amputee subject, for generic activation of the gastrocnemius and corresponding measured EMG activity from an implanted EMG sensor are shown in Table 2. The gastrocnemius is a superficial bipennate muscle in the back part of the lower leg. It runs from its two heads just above the knee to the heel, a two joint muscle. In each of these first and second tests, an initial test was performed and these results are shown in columns M.1-M.5, and the final test results performed five months after the initial tests are shown in columns F.M.1-F.M.5. The activities of both muscles were recorded for each test to identify any co-contraction activity.

TABLE 1

Generic Activation Testing results from activation of the Tibialis Anterior.

| | M. 1 | M. 2 | M.3 | M. 4 | M. 5 | F. M. 1 | F. M. 2 | F.M.3 | F.M. 4 | F.M. 5 |
|---|---|---|---|---|---|---|---|---|---|---|
| Gastroc. | | | | | | | | | | |
| Average | 0.3 | 0.3 | 0.2 | 0.2 | 0.1 | 0.1 | 0.1 | 0 | 0 | 0 |
| Ave. [mV] | 0 | 0 | 0 | 0 | 0 | 0 | 0 | 0 | 0 | 0 |
| Max | 3.6 | 2.8 | 2.8 | 2 | 1.2 | 3.4 | 2 | 1 | 0.6 | 0.2 |
| Max [mV] | 0.3 | 0.2 | 0.2 | 0.2 | 0.1 | 0.3 | 0.2 | 0.1 | 0 | 0 |
| Tib. Ant. | | | | | | | | | | |
| Average | 138.2 | 136.9 | 131.1 | 123.8 | 102.0 | 131.1 | 122.9 | 123.8 | 122.2 | 123.1 |
| Ave. [mV] | 10.8 | 10.7 | 10.3 | 9.7 | 8.0 | 10.3 | 9.6 | 9.7 | 9.6 | 9.7 |
| Max | 177.8 | 172.8 | 173.2 | 170.8 | 152.0 | 183.6 | 171.2 | 165.6 | 168.2 | 171.6 |
| Max [mV] | 13.9 | 13.6 | 13.6 | 13.4 | 11.9 | 14.4 | 13.4 | 13.0 | 13.2 | 13.5 |

The data in Tables 1 and 2 show that this user has better control over the tibialis anterior. For instance, the gastrocnemius co-contracts less while contracting the tibialis anterior. The test data further indicate particular values and ranges of muscle activity EMG signals that may be used for POD control. The EMG sensor outputs a unitless value from 0-255 in proportion to the detected myoelectric activity. The values in the rows for Ave [mV] and Max [mV] indicate corresponding values for the EMG sensor outputs in millivolts.

TABLE 2

Generic Activation Testing results from activation of the Gastrocnemius.

|  | M. 1 | M. 2 | M.3 | M. 4 | M. 5 | F. M. 1 | F. M. 2 | F.M.3 | F.M. 4 | F.M. 5 |
|---|---|---|---|---|---|---|---|---|---|---|
| Gastroc. | | | | | | | | | | |
| Average | 93.3 | 97.1 | 99.4 | 98.0 | 105.0 | 119.9 | 100.4 | 96.5 | 95.9 | 96.9 |
| Ave. [mV] | 7.3 | 7.6 | 7.8 | 7.7 | 8.2 | 9.4 | 7.9 | 7.6 | 7.5 | 7.6 |
| Max | 135.0 | 147.0 | 156.8 | 146.8 | 152.0 | 180.8 | 160.6 | 155.6 | 162.0 | 159.6 |
| Max [mV] | 10.6 | 11.5 | 12.3 | 11.5 | 11.9 | 14.2 | 12.6 | 121 | 12.7 | 12.5 |
| Tib. Ant. | | | | | | | | | | |
| Average | 14.0 | 12.2 | 11.6 | 11.0 | 10.4 | 7.4 | 6.7 | 7.,3 | 6.3 | 7.4 |
| Ave. [mV] | 1.1 | 1.0 | 0.9 | 0.9 | 0.8 | 0.6 | 0.5 | 0.6 | 0.5 | 0.6 |
| Max | 24.2 | 20.4 | 20.0 | 19.8 | 18.8 | 12.6 | 29.0 | 13.8 | 11.0 | 13.8 |
| Max [mV] | 1.9 | 1.6 | 1.6 | 1.6 | 1.5 | 1.0 | 2.3 | 1.1 | 0.9 | 1.1 |

Figure 10A:
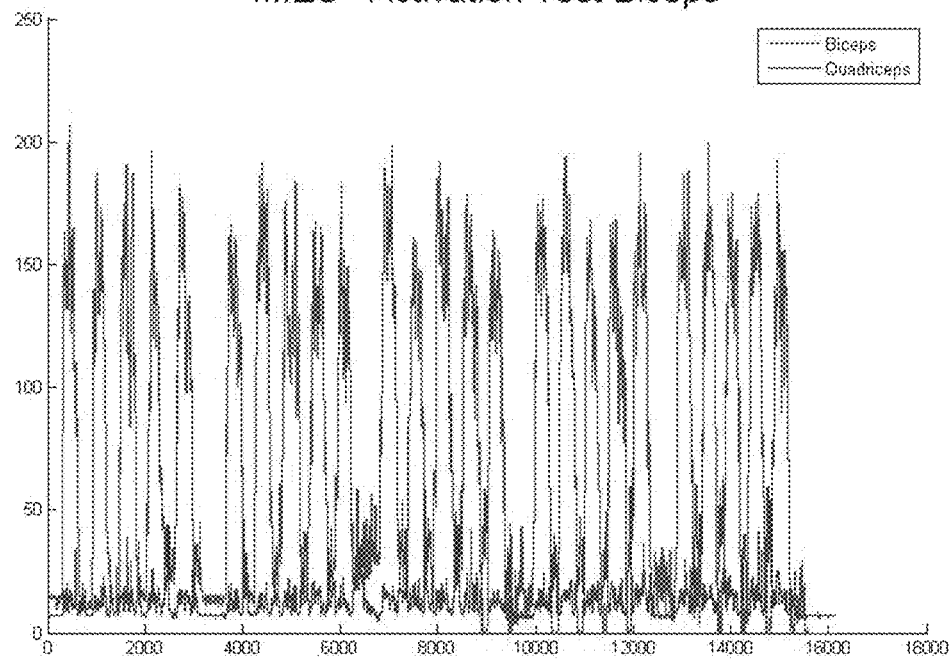
FIGS. 10A-10B are data plots showing experimental results from tests of a transfemoral amputee subject for generic activation of, respectively, the biceps and quadriceps, and corresponding measured EMG activity from an implanted EMG sensor.
Figure 10B:
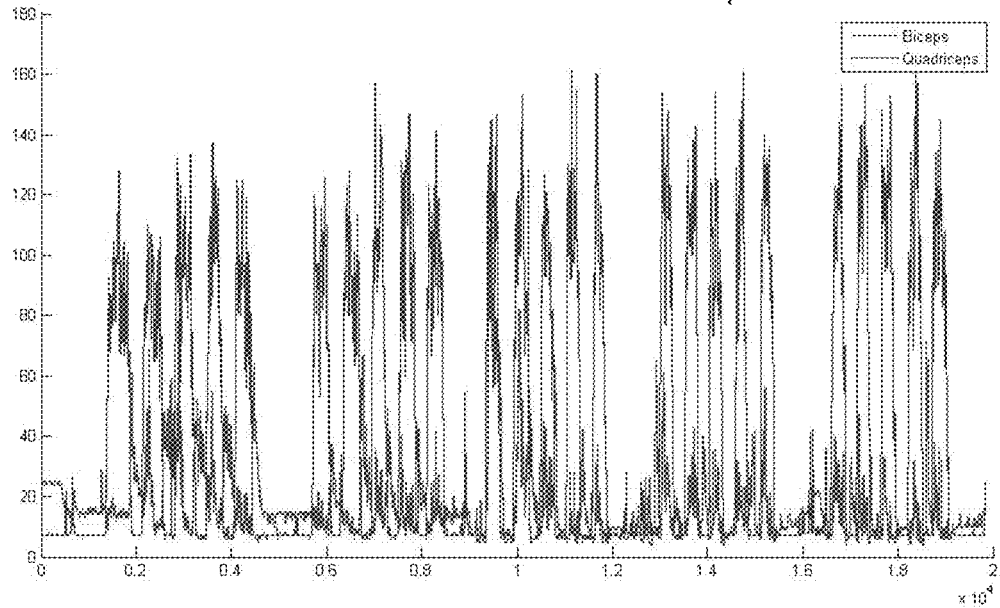

In some embodiments, experimental results from generic muscle activation tests of leg muscles and/or muscles of other body parts may be used. Experimental results from a first test, of a transfemoral amputee subject, for generic activation of the biceps and corresponding measured EMG activity from an implanted EMG sensor are shown in FIG. 10A. Experimental results from a second test, of the same transfemoral amputee subject, for generic activation of the quadriceps and corresponding measured EMG activity from an implanted EMG sensor are shown in FIG. 10B. The test data indicate particular values and ranges of muscle activity EMG signals that may be used for POD control. During both the initial and final assessment testing, the subject was able to produce a good signal from both muscles applicable for control. However the subject demonstrated greater control capability of the biceps during the testing which can be seen during the activation of the quadriceps where the subject co-contracts the biceps. In the final assessment testing the mean amplitude of the quadriceps went down but the subject demonstrated an improved control over the muscle compared with the initial assessment. These are just example data and patterns observed for one set of tests. Other suitable tests and data may be used.

Figure 11A:
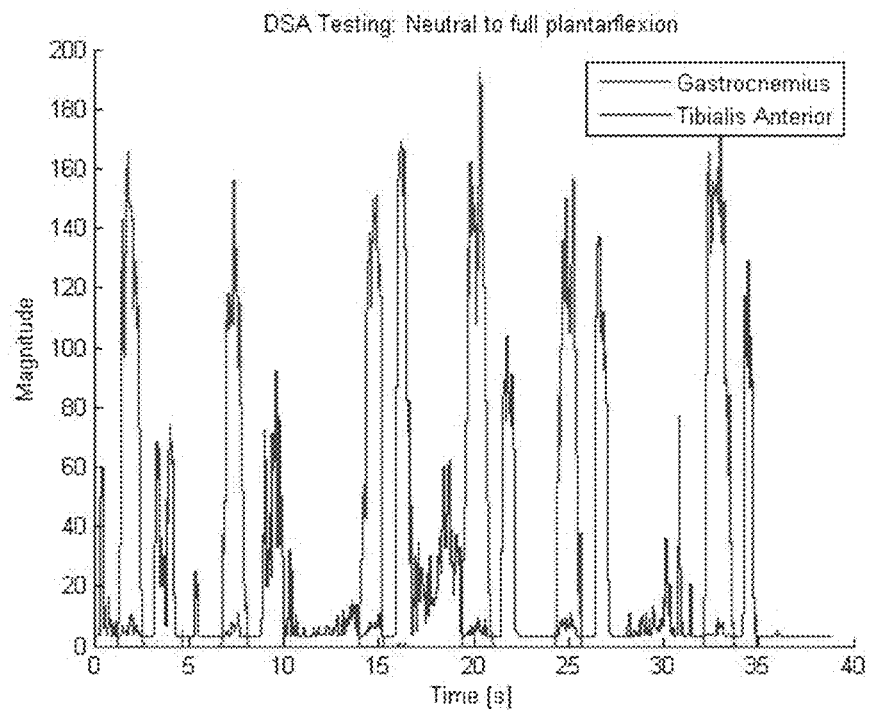
FIGS. 11A-11B are data plots showing experimental results from tests showing muscle activity from specific activation testing for, respectively, voluntary movement of an ankle from neutral to full plantarflexion to neutral and voluntary movement of an ankle from neutral to full dorsiflexion to neutral.
Figure 11B:
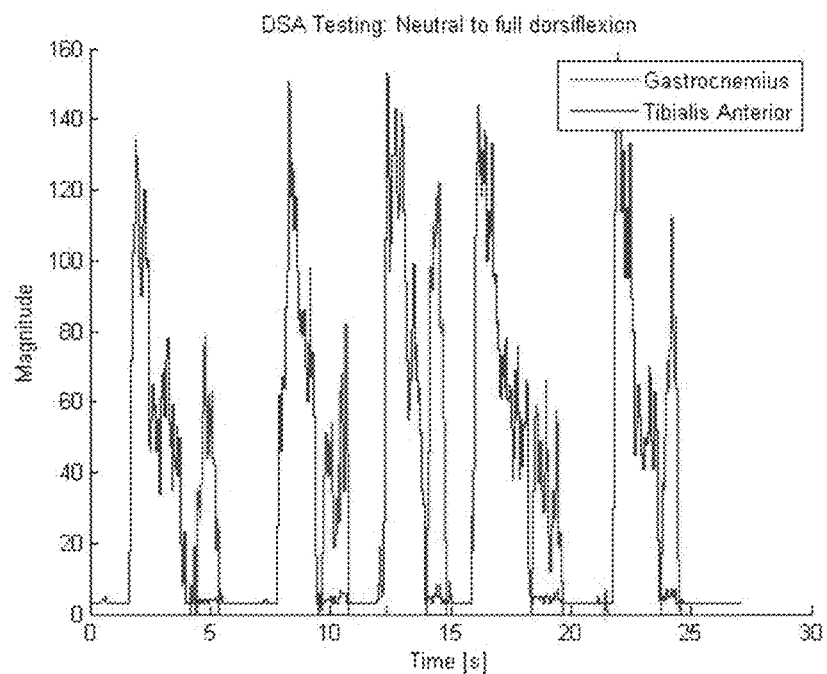

In some embodiments, experimental results from specific activation tests may be used. Experimental results showing activity of the tibialis anterior and of the gastrocnemius during voluntary movement of an ankle device are shown in FIGS. 11A-11B. In FIG. 11A, the data show muscle EMG activity during movement from the neutral position to full plantarflexion and then back to the neutral position. In FIG. 11B, the data show muscle EMG activity during movement from the neutral position to full dorsiflexion and then back to the neutral position. The EMG test data indicate particular values and ranges of muscle activity EMG signals that may be used for control of an ankle POD device, whether voluntary or involuntary.

Figure 12:
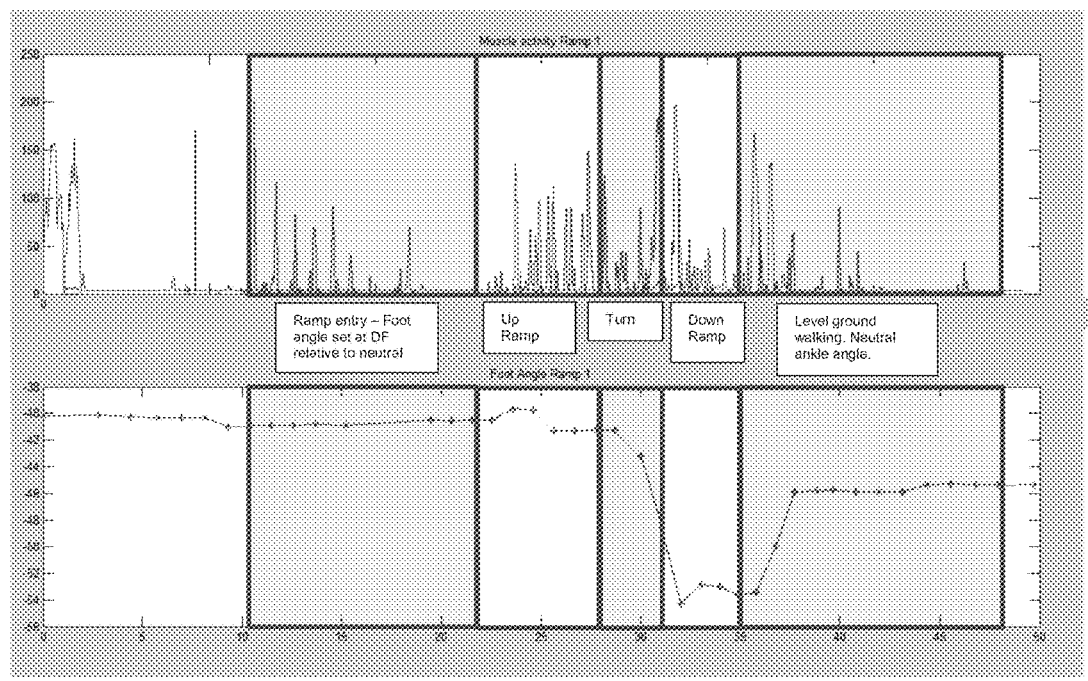
FIG. 12 are data plots showing experimental results from EMG activity (top) of the gastrocnemius (blue) and the tibialis anterior (green) and the corresponding foot angle (bottom) during a ramp activity.

In some embodiments, the various EMG control techniques can be based, in whole or in part, on experimental data showing correlations between muscle activity and joint angle. FIG. 12 depicts two experimental data plots in top and bottom graphs of the figure. FIG. 12 shows experimental data showing EMG activity (top graph) of the gastrocnemius (blue) and the tibialis anterior (green) versus the corresponding foot angle (bottom graph) during an up and down ramp activity. The user walked to the up ramp from about 0 to 11 seconds, entered the ramp from about 11 to 22 seconds, walked up the ramp from about 22 to 29 seconds, turned from about 29 to 31.5 seconds, walked down the ramp from about 31.5 seconds to 36 seconds, and continued level ground walking from about 36 seconds to about 49 seconds.

The EMG test data indicate particular values and ranges of EMG signals from the gastrocnemius and the tibialis anterior, during the various phases of the movement activity, that may be used for EMG-based control of the angle, such as the neutral angle, of an ankle POD device.

The ankle or other joints can be controlled based on the resulting EMG signals in a variety of suitable manners. In some embodiments, lower-limb motor control of an ankle joint can be characterized by both automatic-like control and voluntary-like control systems. In such cases, the bi-modal control system can be replicated to allow direct user control over the joint (e.g., some of its functions or behaviors) in certain contexts while still providing automatic control in other contexts. For example, and without limitation, control of a neutral position of a motorized ankle-foot device can be performed both in bi-modal control (e.g., voluntary and automatic) and in single mode (e.g., direct control, such as with the data shown in FIGS. 11A-11B).

Voluntary Position Control of Ankle Joint

The ankle joint can be controlled using position control where the EMG information is used to identify certain target joint positions. A user can activate different muscles or the same muscle in different ways to dorsi-flex or plantar-flex the ankle joint. In some embodiments, the different muscles can be antagonist muscles. The amplitude and/or the duration of the EMG signal can determine the position to which the ankle joint adjusts. Further, the envelope of the data may be used. For example, a linear envelope may be determined based on the shape of the data over a period of time. Such envelope may be rectangular, square, triangular, trapezoidal, etc. and with varying dimensions. In some cases, the neutral position of the ankle joint can be the position of the ankle joint when there is substantially no muscle activation. This neutral position can change with terrain. For example, the neutral position can be at a different position when the ankle is on a slope than when it is on level ground. Typically, the ankle can be in neutral position during stance. The neutral position can change with each swing, where the POD adjusts the neutral position for the terrain. As a non-limiting example, at the beginning of swing, an ankle POD can perform toe-up from the neutral position. During swing, the POD can move from initial- to mid-swing. In mid-swing, the POD can reach the POD's maximum angle during swing. For example, the mid-swing position can be the largest reading of a gyroscope or angle sensor during swing. Mid-swing can also be the point during swing with the least muscle activity. Based at least in part on the muscle activity, in the form of EMG signals, from toe-off to mid-swing, the POD can determine the neutral position for the next step. For example, and without limitation, the POD can compare EMG signals from antagonistic muscles to determine the neutral position. Such a comparison can indicate the direction of flexion and/or direction of change of neutral position for the next step. Using the determined neutral position, the POD can activate one or more actuators to adjust to the determined neutral position.

In some embodiments, the POD can compare the EMG signal from a muscle (or muscles) with one or more thresholds to determine the neutral position. For example, the POD can compare any one or any combination of characteristics of the EMG signal, such as, but not limited to, amplitude, frequency, envelope, response time, rate of change, etc., with any one or any combination of one or more EMG signal thresholds, such as one, but not limited to, one or more amplitude thresholds, one or more frequency thresholds, one or more envelope thresholds, one or more response time or rate of change thresholds, etc. For example, in some embodiments, the joint can flex or extend more in response to larger EMG signal amplitudes or the EMG signal satisfying different thresholds. Experimental data, such as those described herein, may be used to determine quantities for the appropriate thresholds.

In certain embodiments, the POD, for example the controller, can compare the EMG signal from a muscle (or muscles) with EMG signals from previous steps to determine the neutral position. For example, if the amplitude of the EMG signal of the current step is larger (or smaller) than the amplitude of the EMG signal from a previous step, the POD can flex/extend the joint, etc. It will be understood that any one or any combination of the characteristics of the EMG signal can be used as desired.

In addition, in some embodiments, the POD can use a time series analysis to determine the neutral position. For example, the data set from the window of time can be compared to data sets stored in the controller, which correspond to different neutral positions. Based at least in part on the comparisons, the POD can determine the neutral position. In some embodiments, the data sets stored in the controller can have approximately the same number of data points as the data set from the window of time and/or correspond to approximately the same amount of time as the window of time. Further, measurements from other sensors (e.g., accelerometers, gyroscopes, magnetometers) can be used instead of or in combination with the EMG signal. In some embodiments, the ankle joint can flex or extend more in response to larger EMG signal amplitudes.

The direction of the flex can depend on the relative amplitudes of the EMG signals of the different muscles, or the manner in which a muscle is activated. By way of illustrative example, and without limitation, the following equation can be used to describe the target position (Postarget) based on the EMG signals of muscle X (MuscleXsignal) and muscle Y (MuscleYsignal), and the neutral position (Posneutral). The signals can be adjusted according to gain and offset factors. For example, the signal for muscle X can be multiplied by gain MuscleXgain and offset by offset MuscleXoffset. Similarly, the signal for muscle Y can be multiplied by gain MuscleYgain and offset by offset MuscleYoffset. The equation may be the following:

$$Postarget=Posneutral+(MuscleXsignal*MuscleXgain+MuscleXoffset-MuscleYsignal*MuscleYgain+MuscleYoffset)$$

In some embodiments, at times it may be desirable to remove a component or a muscle signal from the equation. For instance, a particular gain may be set to zero to remove the component or muscle signal. One example equation is provided below:

$$Postarget=Posneutral+(MuscleXsignal+MuscleXoffset)*MuscleXgain-(MuscleYsignal+MuscleYoffset)*MuscleYgain$$

As another example, another position control can have the position control with a floating neutral position (Posneutral) where the EMG signal determines the changed neutral position of the ankle joint. The ankle joint can be moved, for example with a constant speed, to a target position (Postarget). The target position can be determined by the EMG signal of muscle X (MuscleXsignal) and muscle Y (MuscleYsignal) and the current position (Poscurrent). Again, the signal for muscle X can be multiplied by gain MuscleXgain and offset by offset MuscleXoffset. Similarly, the signal for muscle Y can be multiplied by gain MuscleYgain and offset by offset MuscleYoffset. The control loop can move the ankle joint to stay in the neutral position. Thus, Postarget can be equal to Posneutral. This calculation is summarized in the below equation:

$$Postarget=Posneutral=Poscurrent+(MuscleXsignal*MuscleXgain+MuscleXoffset-MuscleYsignal*MuscleYgain+MuscleYoffset)$$

In some embodiments, it may be desirable to remove a component or a muscle signal from the equation. For instance, a particular gain may be set to zero to remove the component or muscle signal. One example equation is provided below:

$$Postarget=Posneutral=Poscurrent+(MuscleXsignal+MuscleXoffset)*MuscleXgain-(MuscleYsignal+MuscleYoffset)*MuscleYgain$$

In some cases, the target position can be based on the signal from one muscle. For example, the controller can ignore the muscle signal with lower EMG signal amplitudes or only one sensor can be used. In embodiments, where one muscle is used, the user can activate the muscle in different patterns, amplitudes, or durations to control the direction of the flexion and/or the position to which the joint adjusts. For example, activating the muscle for a relatively short amount of time but with a relatively large amplitude can cause the ankle to dorsi-flex, whereas activating the muscle for a relatively long amount of time but with a relatively small amplitude can cause the ankle to plantar-flex, etc. In certain cases, multiple activations of the muscle within a period of time can be used to control the direction and/or speed of the flexion, etc. Also, a person having ordinary skill in the art should appreciate that the above equations can be adapted to calculate the target position based on a plurality of muscle signals, including a number of muscle signals greater than two.

Voluntary Velocity Control of Ankle Joint

In some embodiments, an ankle joint can be controlled using velocity control where the EMG information is used to identify certain target joint velocities. A user can activate different muscles (for example, antagonist muscles, or other muscles), or the same muscle in different ways, to dorsi-flex or plantar-flex the ankle joint. The amplitude of the EMG signal can determine the velocity of the ankle joint. In some cases, no muscle activation (e.g., an EMG signal with a smaller to substantially zero amplitude) can cause the velocity of the ankle joint to be zero. In certain cases, the joint can flex faster with higher EMG signal amplitudes. Again, the direction of the flex can depend on the relative amplitudes of the EMG signals of muscle(s) being used to control the POD. The below equation describes a non-limiting example of this relationship, where the variables are as identified above.

$$Postarget = Poscurrent*(MuscleXsignal*MuscleXgain+\\MuscleXoffset-MuscleYsignal*MuscleYgain+\\MuscleYoffset)$$

The equation describes the position control with two muscles MuscleX and MuscleY and how their activation can influence the target position (Postarget). In some cases, the target position can be based on only the EMG signal from one muscle. For example, the controller can ignore the muscle signal with lower EMG signal amplitude or use only one sensor. Also, a person having ordinary skill in the art should appreciate that the above equations can be adapted to calculate the target position based on a plurality of muscle signals, including a number of muscle signals greater than two.

Controlling the Ankle Joint while Ambulating with Muscle Activation

In some embodiments, a user of a microprocessor prosthetic ankle ("MPA") can change the neutral position to adapt to different terrains using muscle activation information. The MPA can perform gait analysis of the user using various sensors (e.g. accelerometer, gyroscope, and/or magnetometer). The gait analysis can provide the MPA with the gait phases and gait events. In some cases, a window of control can be used during a gait for the user to change the neutral position of the ankle joint. In one setup, the control window can start at the beginning of the swing phase and closes at mid-swing. The window can also close at other motion-related events, such as, without limitations, heel strike, toe down, heel off, toe off, mid-swing, or end of swing. Within the control window, the muscle activations can be read and accumulated. At the end of the control window, the controller can further process the accumulated data and establish a change in the neutral position. For example, and without limitation, based at least in part on the EMG signals from toe-off to mid-swing, the POD can determine the neutral position for the next step. Such accumulated data can be relative EMG signals from antagonistic muscles, from a single muscle, etc., as described above. Furthermore, the ankle joint can be moved to the newly calculated neutral position. These actions can be performed in every swing phase.

Automatic Control of the Ankle Joint while Ambulating

In some embodiments, an MPA can have an automatic control that can be used in combination with muscle activation voluntary control and/or other features described in this disclosure. The automatic control can perform toe-lift operations while the ankle joint is ambulating. In some cases, this combination can increase safety and decrease mental load for the user. The MPA can then dorsi-flex the ankle joint several degrees at the start of the swing phase and return to the neutral position at the mid-swing event.

The MPA can also merge the controls from the user muscle activation with the automatic control for the neutral angle. The merged control can be scalable from the user being able to completely override the automatic control or the automatic control can completely override the user control, or anywhere in-between the aforementioned extremes.

In some embodiments, a POD having a powered ankle device may be used. For example, the powered ankle by Spring Active, Inc. (Tempe, Ariz.) may be used. In some embodiments, muscle activation may effect powered plantar-flexion of the ankle device. In some embodiments, such powered plantar-flexion may be controlled in part with direct control and in part with automatic control. For instance, the user may initiate powered plantar-flexion with muscle activation and the control system may enter a state where the ankle controller automatically continues effecting plantar-flexion (e.g. in late swing) or powered plantar-flexion (e.g. in late stance) while in that state (for example in running). As another example, the user may initiate direct control plantar-flexion during swing in stair descent, and after initiation the automatic control of plantar-flexion takes over while in stair descent state. The state may be exited by direct control, e.g. muscle activated dorsi-flexion while in stair descent. The amount of plantar-flexion and/or powered plantar-flexion can be based on the adjusted neutral angle, such as the adjusted ankle neutral angle. These are just some examples of the types of activities that may incorporate such control techniques, and other suitable activity types may incorporate the control techniques as well.

Controlling the Ankle Joint while Non-Ambulating with Muscle Activation

In some embodiments, the user of an MPA can change the neutral position at any time with muscle activation while the user is not ambulating. Such functionality can be desirable if the user wants to set the ankle joint to a certain position for certain tasks. For example, the user may want to dorsi-flex the ankle joint to a certain position to stand up from a chair more easily. A control loop can be used to set the ankle joint to the determined neutral position when the user is not ambulating.

Click Control of Gait State or Terrain Transition in Prosthetics Using EMG Information A click can include activating one or more muscles for a certain amount of time. Triggering a click or a combination of a single, double, triple, short and/or long clicks can provide a prosthesis with information about the intent of the user to transition from one state and/or terrain to another state and/or terrain, or to dorsi-flex or plantar-flex. In some cases, the click can be a threshold for triggering a transition. For example, and without limitation, the threshold can be a predefined amplitude threshold where if the EMG signal for a muscle exceeds the predefined amplitude threshold, a controller of the POD can identify a transition. As another example, the threshold can be a predefined frequency threshold, where if the EMG signal for a muscle exceeds the predefined frequency threshold, a controller of the POD can identify a transition. As such, a user can intentionally transition to another state and/or terrain, giving the user a greater feeling of control of the prosthesis. The user can invoke the transition both while being mobile and immobile. For example, and without limitation, the user can invoke the transition during stair ascent/descent, walking, ramp ascent/descent, and/or while standing/sitting.

Modulation of Mechanical Impedance Based on EMG Information

In some embodiments, the POD can dynamically adjust mechanical impedance. For example, and without limitation, the POD can dynamically increase or decrease the damping for an actuator. In some embodiments, actuators can be at least one of a drive motor, a hydraulic actuator, magneto-rheological actuator, and/or any actuator used for actuating a joint (e.g., a knee or ankle) of a POD. The POD can also increase the stance flexion stiffness for knees based on an EMG signal. The EMG signal can also be used to dynamically adjust the joint impedance. For example, and without limitation, a controller of the POD can use an EMG signal to identify an activity that requires more stability and less flexion of a knee. As a result, the impedance of the knee joint can be increased/decreased to resist movement. The POD can calibrate impedance to the amplitude of the EMG signal during a particular activity. For example, and without limitation, the POD can monitor the EMG signal of a muscle while the user is walking. In some cases, when the POD measures EMG signals with increased amplitudes, it can provide higher resistance in response. In some cases, the relationship between the amplitude of the EMG signal and the impedance is linear where the impedance is proportional to the amplitude of the EMG signal with a baseline offset. In some cases, the baseline offset can be a calibrated value representing the amplitude of the EMG signal at any position desired by the user to have no actuator impedance. For example and without limitation, the baseline offset can be the EMG signal amplitude when the user is not moving, such as in stance mode.

In some embodiments, EMG signals can be used for powered ankle movements such as plantarflexion and dorsiflexion. For example, and without limitation, an actuator can be coupled to the ankle of a POD. The actuator can actuate the ankle for plantarflexion and/or dorsiflexion based at least in part on the magnitude of the EMG signals from antagonistic muscles, as described above and/or based on muscle activity during late stance. In some cases, the POD can actuate the ankle based on the pattern of the EMG signal, including, without limitation, the EMG signal's minimum, maximum, average amplitude, slope, frequency, etc. In some cases, the POD can also use a dynamic library comprising identified EMG signal patterns and compare monitored EMG signal patterns to the identified EMG signal patterns. The actuator of the POD can deliver variable power and/or variable resistance for ankle movements related to activities such as chair exit, level ground walking, slope walking, and/or jumping. For example and without limitation, the POD can recognize that the POD is in a chair sit mode. When the amplitude of the EMG signals associated with certain muscles, such as antagonistic muscles used for ankle control, satisfies an amplitude threshold (for example, is equal to or less than the EMG signal threshold, or greater than the EMG signal threshold), the POD can power and/or provide the resistance for the ankle for a chair exit. Similar systems and methods can be used while the user is walking. For example and without limitation, the POD can recognize that the POD is in a walking mode. The POD can monitor if patterns in EMG signals from certain muscles, such as antagonistic muscles for ankle control, satisfy an amplitude threshold (for example, is equal to or less than the EMG signal threshold, or greater than the EMG signal threshold). If so, the ankle can power and/or provide the resistance for changing walking slopes and/or jumping.

Transitions

Signals (e.g., EMG signals) can be used to transition prosthesis functionality from one activity to another. For example, and without limitation, a controller can analyze an EMG signal to determine transitions as described in the Voluntary Control section, Involuntary Control section, and throughout this disclosure. For example, the following activities can be activated and controlled by an EMG signal. In some cases, a controller can also take into account other measurements in determining when to transition. For example, the trigger condition for transition can be a combination of the EMG signal and/or measurements taken by a ground force sensor, inertial sensor and/or joint angle position sensor. AI, hardware, and/or software can balance these factors and determine when to transition.

In some embodiments, a controller can issue a control signal to control an actuator. For example, the controller can use an EMG signal as a driving signal for actuators when going from one activity to another. The control signal can be purely related to the EMG signal, a function of the EMG signal, and/or a combination of the EMG signal and measurements by the inertial sensor, the ground force sensor, the joint angle sensor, and/or the joint moment sensor. The control signal can be used to decide the amount and/or kind of assistance provided from the actuators when standing up, or control the speed of the process.

Sit-to-Stand Activity

In some embodiments, an EMG signal can be used for actuator activation to transition from a sit-to-stand activity. For example, an EMG signal can be used to trigger a prosthesis to stand up from a seated position by using a predefined threshold. For example, and without limitation, the threshold can be a predefined amplitude threshold where if the EMG signal for a muscle exceeds the predefined amplitude threshold, a controller of the POD can identify a transition. As another example, the threshold can be a predefined frequency threshold, where if the EMG signal for a muscle exceeds the predefined frequency threshold, a controller of the POD can identify a transition. Once the EMG signal exceeds the predefined amplitude and/or frequency threshold values, the prosthesis transitions to a standing up state. Relative measurements can also be used where the amplitude of an EMG signal in one instance of time can be compared to the amplitude of the EMG signal at another instance of time. For example, and without limitation, in some cases, an EMG signal measured from a muscle at rest can be smaller in amplitude than the EMG signal measured from that same muscle during contraction. A stronger contraction can have an amplitude larger than a smaller contraction. As desired, a POD can associate a change in amplitude from one instance of time to the amplitude at another instance in time as indicative of a transition from one activity to another. For example, a user who is about to stand up from sitting can have a muscle contraction much larger than any contraction he had while sitting. The POD can recognize that proportionally larger contraction and transition from sitting to standing. In some cases, recognizing the larger contraction can be in the form of a proportion threshold, where if the proportion between the amplitude of an EMG signal at one instance of time and another instance of time exceeds the proportion threshold, the POD can recognize a particular transition. As previously mentioned, the transition can depend on a combination of the EMG signal and/or other measurements by other sensors (e.g., accelerometers, inertia sensors, gyroscopes, magnetometers, pressure sensors, and/or any other sensors described in this disclosure). In some embodiments, the AI can take into account patterns in the EMG signal and/or other measurements to determine a transition. For example, and without limitation, an accelerometer can also be used to detect the user's transition from sitting still to moving to stand up.

In some cases, a control signal can be issued (e.g., by the controller) to the actuator to cause it to actuate the POD from a seated position to a standing position. As previously mentioned, the control signal can depend on a combination of the EMG signal and/or other measurements. The control signal can be used to decide the assistance provided from the actuators when standing up or control the speed of the process.

Stand-to-Sit Activity

In some embodiments, an EMG signal can be used for actuator activation to transition from a standing to a sitting activity. In some cases, once the EMG signal exceeds a predefined threshold value the prosthesis should transition to a sit down state. For example, and without limitation, the threshold can be a predefined amplitude threshold where if the EMG signal for a muscle exceeds the predefined amplitude threshold, a controller of the POD can identify a transition. As another example, the threshold can be a predefined frequency threshold, where if the EMG signal for a muscle exceeds the predefined frequency threshold, a controller of the POD can identify a transition. Again, as described above, the POD can also recognize a transition based at least in part on a proportional change in EMG signals in one instance of time as compared to another instance of time. For example, when in stance phase, the POD can recognize an EMG signal with a proportionally larger EMG signal as indicative of a muscle contraction for transitioning into sitting mode. As previously mentioned, the transition can depend on a combination of the EMG signal and/or other measurements by other sensors (e.g., accelerometers, inertia sensors, gyroscopes, magnetometers, pressure sensors, and/or any other sensors described in this disclosure). Again, in some embodiments, the AI can take into account patterns in the EMG signal and/or other measurements to determine a transition. For example, and without limitation, an accelerometer can also be used to detect the user's transition from standing still to sit down based on movement.

In some cases, a controller can issue a control signal to the actuator to cause the actuator to actuate the POD from a standing position to a seated position. As previously mentioned, the control signal can depend on a combination of the EMG signal and/or other measurements. In some embodiments, the control signal can vary the resistance in the actuators during sitting down. In some embodiments, proportional control may be used that is activated after a stand-to-sit or sit-to-stand motion has been identified to, for example, directly control a Power knee.

Walking

In some embodiments, an EMG signal can be used for actuator activation to transition to a walking mode from a standing position. A combination of the EMG signal exceeding a frequency and/or amplitude threshold and/or one or more of measurements taken by a ground force sensor, joint angle sensors, and/or joint moment sensor can be used to distinguish between the user shuffling weight to/from the prosthesis and committing to walking.

In some embodiments, an EMG signal can be used to trigger the prosthesis to stop flexion while in swing phase while walking. A combination of the EMG signal exceeding a frequency and/or amplitude threshold and/or one or more measurements taken by a ground force sensor, joint angle sensors, and/or joint moment sensor can be used to determine the maximum flexion while walking. Again, as described above, the POD can also recognize a transition based at least in part on a proportional change in EMG signal in one instance of time as compared to another instance of time. For example, if the amplitude of an EMG signal at one instance of time is a certain proportion as compared to the amplitude of the EMG signal at other points of time, the POD can recognize a transition into walking mode. Again, in some embodiments, the AI can take into account patterns in the EMG signal and/or other measurements to determine a transition. For example, and without limitation, an inertia sensor (e.g., an inertia measurement unit ("IMU") can also be used to detect the user's transition from standing to walking.

In some embodiments, an EMG signal can be used to generate a control signal for determining the amount of stance flexion at heel strike. The EMG signal can be used in combination with joint angle and/or joint moment sensors.

In some embodiments, an EMG signal can be used to trigger the prosthesis to go from a high resistance behavior to either knee flexion motion or low knee resistance behavior. The EMG signal can be used in combination with one or more measurements of a joint angle sensor, joint moment sensor, inertial sensor and/or ground force sensor.

The EMG signal can also be used to control the amount of resistance a knee, or other joint, provides during flexion while walking up or down an inclination. For example, and without limitation, the EMG signal can be measured from one or more muscles, such as antagonistic muscles. The relative amplitudes of the EMG signals from the muscles can be used to actuate the knee one way or the other to control the knee angle. For example, the POD can measure EMG signals from the quadriceps and hamstring. A relatively large signal from the quadriceps as compared to the hamstring can flex the knee back (e.g., dorsally), whereas a relatively large signal from the hamstring as compared to the quadriceps can flex the knee forward (e.g., ventrally). Based on the relative amplitudes of the EMG signals, the POD can monitor and determine the terminal position of the knee while walking. Knee impedance can also be controlled as described elsewhere in this disclosure, such as by comparing EMG signals from a muscle (or muscles) with one or more thresholds, previous EMG signals, time series analysis, etc. Again, the EMG signal can be used alone or in combination with other onboard sensors.

In some cases, while walking or in any other activity described in this disclosure, a POD can identify a stumble and/or slip by the user. A stumble and/or slip can be identified by a rapidly changing and/or erratic EMG signal. For example, and without limitation, a slip during gait can be identified by a sudden erratic signal in an otherwise steady pattern.

Standing

In some embodiments, an EMG signal can be used to control a knee joint position. The EMG signal can be used to control the position of the knee while standing, for example and without limitation, while leaning against a wall. In such cases, a POD can measure EMG signals from one or more muscles, such as antagonistic muscles. The relative amplitudes of the EMG signals from the muscles can be used to actuate the knee one way or the other to control the knee angle, as described in this disclosure. Knee impedance can also be controlled as described in this disclosure. The EMG signal would allow a user to receive actuator assistance when extending the knee joint and/or allow the knee to provide less resistance when flexing the joint.

Stairs

An EMG signal can be used to trigger the prosthesis to enter a stair climbing mode or stair descent mode. A combination of the EMG signal exceeding a frequency and/or amplitude threshold and/or one or more measurements taken by a ground force sensor, joint angle sensors, and/or joint moment sensor can be used to determine when the prosthesis is entering a stair climb mode or a stair descent mode. Again, as described above, the POD can also recognize a transition based at least in part on a proportional change in EMG signal in one instance of time as compared to another. For example, if the amplitude of an EMG signal at one instance of time is a predetermined proportion as compared to the amplitudes of EMG signals at other points of time, the POD can recognize a transition into stair climbing mode or stair descent mode. Again, in some embodiments, the AI can take into account patterns in the EMG signal and/or other measurements to determine the transitions. For example, and without limitation, an inertial sensor (e.g., an inertial measurement unit ("IMU")) can also be used to detect the user's transition to climbing stairs or descending stairs.

Again, an EMG signal can be measured from one or more muscles, such as antagonistic muscles. The relative amplitudes of the EMG signals from the muscles can be used to actuate the knee one way or the other to control the knee angle as described in this disclosure. Based on the relative amplitudes of the EMG signals, the POD can monitor and determine the terminal position of the knee on a slope, such as during slope ascent and slope descent.

In some embodiments, an EMG signal can be used to control the amount of assistance or impedance, as is described in this disclosure, the knee provides during extension while climbing steps or descending steps. Again, the EMG signal can be used in combination with other onboard sensors.

AI Training

In some embodiments, the AI can be trained to associate EMG signals and/or other measurements with certain activities. In some cases, the AI training can be done through a training mode where the user tells the AI what the user is doing in a user interface, and the AI can monitor EMG signals and/or measurements from other sensors during performance of the activity in order to learn to recognize the signals generated by the patient during that activity. For example, and without limitation, the user can indicate that the user is performing any of the activities described in this disclosure, and the AI can monitor the EMG signals and signals from other sensors during those activities.

In some embodiments, the AI can gradually learn to associate EMG signal patterns and/or other sensor signal patterns with certain activities. For example, and without limitation, in some cases, the AI can already identify an activity based on one or more sensors (e.g., EMG, accelerometers, inertia sensors, gyroscopes, magnetometers, pressure sensors, and/or any other sensors described in this disclosure). The AI can then monitor other sensors during those activities in order to learn to associate patterns in the signals from those sensors with the activities. For illustrative purposes, an AI can know that a user is ascending stairs based at least in part on measurements taken by a gyroscope. During that ascending stairs activity the AI can monitor the EMG signals and associate the EMG signal patterns that it reads during the activity with an ascending stairs activity.

In some embodiments, activities that a user initially activated by active control, such as a click or particular pattern of intentional muscle contraction by the user, can later be controlled by a POD using involuntary control. In such cases, the POD can learn to associate EMG patterns with activities that a user previously identified based on active control. For example, and without limitation, once the user identifies an activity with active control, the POD can monitor the EMG signal patterns during the activity in order to learn when to switch to that activity based on involuntary EMG signal patterns. Similarly, the POD can monitor measurements taken by other sensors and learn to associate patterns in those signals with the activities alone or in combination with the EMG signals. For example, when learning to identify a particular activity, the POD can monitor EMG signals, acceleration signals, and/or angle sensor signals to identify different activities. In some embodiments, the combination of features can increase the ability of the POD to accurately identify the different activities.

In some embodiments, the AI can also learn short-term and/or long-term changes in EMG signals and/or other measurements. For example, and without limitation, muscle growth can cause changes in EMG signals measured from those muscles. Similarly, muscle degeneration can cause changes in EMG signals measured from those muscles. The AI can learn over time to recognize those changes in EMG signals and/or other measurements, and recalibrate its pattern recognition to account for those changes.

In some embodiments, the AI monitors an activity a certain number of times before it acts on a signal. For example, the AI can first monitor the EMG signal of ascending stairs 5, 10, 20, 30, 100, 1000, and/or any desired number of times before it will go into stair ascent mode based at least in part on the EMG signal pattern it observed while monitoring the EMG signal in stair ascent.

The AI can also learn to update and/or associate other signals from other sensors based on similar learning. In this way, the AI can advantageously become more robust and/or more accurate in identifying activities because it can identify those activities based at least in part on more data.

A person/one having ordinary skill in the art would understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof. A person/one having ordinary skill in the art would further appreciate that any of the various illustrative logical blocks, modules, controllers, means, circuits, and algorithm steps or blocks described in connection with the aspects disclosed herein can be implemented as electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both. To clearly illustrate this interchangeability of hardware and software, various illustrative components, blocks, modules, circuits, and steps or blocks have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present disclosure.

The various illustrative logical blocks, modules, and circuits described in connection with the aspects disclosed herein and in connection with the figures can be implemented within or performed by an integrated circuit (IC), an access terminal, or an access point. The IC can include a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and can execute codes or instructions that reside within the IC, outside of the IC, or both. The logical blocks, modules, and circuits can include antennas and/or transceivers to communicate with various components within the network or within the device. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration. The functionality of the modules can be implemented in some other manner as taught herein. The functionality described herein (e.g., with regard to one or more of the accompanying figures) can correspond in some aspects to similarly designated "means for" functionality in the appended claims.

If implemented in software, the functions can be stored on or transmitted over as one or more instructions or code on a computer-readable medium. The steps or blocks of a method or algorithm disclosed herein can be implemented in a processor-executable software module which can reside on a computer-readable medium. Computer-readable media includes both computer storage media and communication media including any medium that can be enabled to transfer a computer program from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm can reside as one or any combination or set of codes and instructions on a machine readable medium and computer-readable medium, which can be incorporated into a computer program product.

It is understood that any specific order or hierarchy of steps or blocks in any disclosed process is an example of a sample approach. Based upon design preferences, it is understood that the specific order or hierarchy of steps or blocks in the processes can be rearranged while remaining within the scope of the present disclosure. Any accompanying method claims present elements of the various steps or blocks in a sample order, and are not meant to be limited to the specific order or hierarchy presented.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system for controlling a prosthetic or orthotic device (POD), the system comprising:
a first limb member;
a second limb member coupled to the first member, the first limb member and the second limb member forming a joint having a neutral position that is used throughout a gait cycle to adjust a joint angle between the first limb member and the second limb member;
at least one first sensor configured to measure electromyography (EMG) signals from a first muscle over a period of time;
a controller configured to receive a first EMG signal from the at least one first sensor and to determine an adjusted neutral position based at least in part on the first EMG signal; and
at least one actuator communicatively coupled to the controller, the at least one actuator configured to actuate the first limb member with respect to the second limb member such that the adjusted neutral position is used throughout the gait cycle to adjust the joint angle between the first limb member and the second limb member.

2. The system of claim 1, further comprising at least one second sensor configured to measure EMG signals from a second muscle over the period of time, wherein the controller is further configured to receive a second EMG signal from the at least one second sensor and to determine an adjusted neutral position based at least in part on the first EMG signal and the second EMG signal.

3. The system of claim 2, wherein the first muscle is antagonistic to the second muscle.

4. The system of claim 1, wherein the at least one first sensor is an external sensor, a subcutaneous sensor, an intraperitoneal sensor, an epimysial sensor, or an intramuscular sensor.

5. The system of claim 2, wherein the at least one first sensor is an external sensor, a subcutaneous sensor, an intraperitoneal sensor, an epimysial sensor, or an intramuscular sensor, and wherein the at least one second sensor is an external sensor, a subcutaneous sensor, an intraperitoneal sensor, an epimysial sensor, or an intramuscular sensor.

6. The system of claim 1, wherein the joint is an ankle joint and the joint angle is an ankle angle.

7. The system of claim 1, wherein the controller is configured to determine the adjusted neutral position in response to determining that the first EMG signal was produced by one or more voluntary contractions of the first muscle.

8. The system of claim 7, wherein the joint is an ankle joint, and wherein the controller is configured to determine a plantar-flexion movement or a powered plantar-flexion movement of the ankle joint based at least in part on the first EMG signal.

9. The system of claim 8, wherein the controller is configured to determine a first state has been entered based at least in part on the first EMG signal, and wherein the controller is configured to automatically effect the plantar-flexion movement or the powered plantar-flexion movement of the ankle joint after entering the first state.

10. The system of claim 9, wherein the first state is running or stair descent.

11. The system of claim 1, wherein the controller is configured to determine the adjusted neutral position based on comparison of the first EMG signal with one or more thresholds.

12. The system of claim 11, wherein the one or more thresholds is one or more of amplitude, frequency, envelope, or rate of change.

13. The system of claim 1, wherein the controller is configured to determine the adjusted neutral position based on comparison of the first EMG signal with previous EMG signals from previous steps.

14. The system of claim 1, wherein the controller is configured to determine the adjusted neutral position based on a time series analysis of the first EMG signal.

15. The system of claim 2, wherein the controller is configured to determine a target position based on the adjusted neutral angle according to the following equation, wherein the first muscle is MuscleX and the second muscle is MuscleY: Postarget=Posneutral=Poscurrent+(MuscleXsignal*MuscleXgain+MuscleXoffset−MuscleYsignal*MuscleYgain+MuscleYoffset).

16. A system for controlling a prosthetic or orthotic device (POD), the system comprising:
a first limb member;
a second limb member coupled to the first member, the first limb member and the second limb member forming a joint having a neutral position that is used throughout a gait cycle to adjust a joint angle between the first limb member and the second limb member;
at least one sensor configured to measure electromyography (EMG) signals associated with a muscle over a period of time;
a controller configured to receive the EMG signal and to determine an adjusted neutral position based at least in part on at least the EMG signal and to select a control mode for POD motion from a plurality of control modes based at least in part on at least the EMG signal; and
at least one actuator communicatively coupled to the controller, the at least one actuator configured to actuate the POD based at least in part on the control mode for POD motion and to actuate the first limb member with respect to the second limb member such that the adjusted neutral position is used throughout the gait cycle to adjust the joint angle between the first limb member and the second limb member.

17. The system of claim 16, wherein the control mode for POD motion is at least one of activation, stair ascent, stair descent, ramp ascent, ramp descent, golfing, biking, Nordic walking, walking, jogging, running or kicking.

18. The system of claim 16, wherein the joint is an ankle joint.

19. The system of claim 16, wherein the EMG signals are associated with voluntary contraction of the muscle.

20. The system of claim 19, wherein the joint is an ankle joint, and wherein the controller is configured to determine a plantar-flexion movement or a powered plantar-flexion movement of the ankle joint based at least in part on the first EMG signal.

21. The system of claim 20, wherein the controller is configured to automatically effect the plantar-flexion movement or the powered plantar-flexion movement of the ankle joint while in the first mode.

22. The system of claim 16, wherein the controller is configured to determine the adjusted neutral position in response to determining that the first EMG signal was produced by one or more voluntary contractions of the first muscle.

23. A system for controlling a prosthetic or orthotic device (POD) including a first limb member and a second limb member forming an ankle joint having a neutral position that is used throughout a gait cycle to adjust an ankle joint angle, the system comprising:
    at least one first sensor configured to be implanted in a muscle and to measure myoelectric signals from the muscle over a period of time and to transmit an electromyography (EMG) signal generated at least in part from the measured myoelectric signals from the muscle;
    at least one second sensor configured to measure at least one of acceleration, angle, force, and velocity over the period of time and to transmit an information signal generated at least in part from the at least one of acceleration, angle, force, and velocity;
    a controller configured to:
        receive the EMG signal and the information signal,
        based at least in part on a determination that the EMG signal does not satisfy an EMG signal threshold, generate a control signal according to a first control scheme, wherein the first control scheme is based at least in part on the information signal,
        based at least in part on a determination that the EMG signal satisfies the EMG threshold, generate the control signal according to a second control scheme, wherein the second control scheme is based at least in part on the information signal and the EMG signal, and
        determine an adjusted neutral position of the ankle joint based at least in part on the EMG signal; and
    at least one actuator coupled to the controller, the at least one actuator configured to actuate the POD based at least in part on the control signal and on the adjusted neutral angle.

24. The system of claim 23, wherein the controller is further configured to determine the control signal based on either the EMG signal or the information signal, wherein the controller chooses between the EMG signal and the information signal based at least in part on the relative amplitudes of the EMG signal and the information signal.

25. The system of claim 23, wherein the controller is further configured to determine the control signal based on either the EMG signal or the information signal, wherein the controller chooses between the EMG signal and the information signal based at least in part on the relative frequency of the EMG signal and the information signal.

26. The system of claim 23, wherein the controller generated control signal comprises information derived from the EMG signal and the information signal.

\* \* \* \* \*

UNITED STATES PATENT AND TRADEMARK OFFICE
CERTIFICATE OF CORRECTION

| | |
|---|---|
| PATENT NO. | : 9,883,815 B2 |
| APPLICATION NO. | : 15/132015 |
| DATED | : February 6, 2018 |
| INVENTOR(S) | : Einarsson et al. |

It is certified that error appears in the above-identified patent and that said Letters Patent is hereby corrected as shown below:

In the Specification

In Column 4 at Line 53, Change "segment;" to --segment.--.

In Column 8 at Line 18, Change "exited." to --excited.--.

In Column 19 at Line 55, Change "bicepts" to --biceps--.

In Column 19 at Line 55, Change "bicepts" to --biceps--.

In Column 19 at Lines 56-57, Change "satorius, lliopsoas," to --sartorius, iliopsoas,--.

In Column 20 at Line 1, Change "brachio radialis," to --brachioradialis,--.

In Column 20 at Line 1, Change "brachil," to --brachii,--.

In Column 24 at Line 66, Change "MATHODS" to --METHODS--.

In Column 25 at Line 62, Change "an and" to --and an--.

In Column 26 at Line 28, Change "hb" to --hub--.

In Columns 29-30 at Line 8 (approx.), Change "121" to --12.2--.

In Columns 29-30 at Line 11 (approx.), Change "7.,3" to --7.3--.

In Column 34 at Line 11, Change "exited" to --excited--.

Signed and Sealed this
Twenty-fourth Day of July, 2018

Andrei Iancu
*Director of the United States Patent and Trademark Office*